(12) United States Patent
Besson et al.

(10) Patent No.: US 9,394,247 B2
(45) Date of Patent: Jul. 19, 2016

(54) METHOD FOR PREPARING A SULFONIMIDE COMPOUND AND SALTS THEREOF

(71) Applicant: RHODIA OPERATIONS, Paris (FR)

(72) Inventors: Bernard Besson, Miribel-les Echets (FR); Francois Metz, Irigny (FR); Olivier Buisine, Saint-Genis-Laval (FR)

(73) Assignee: RHODIA OPERATIONS, Paris (FR)

( * ) Notice: Subject to any disclaimer, the term of this patent is extended or adjusted under 35 U.S.C. 154(b) by 0 days.

(21) Appl. No.: 14/416,939

(22) PCT Filed: Jul. 11, 2013

(86) PCT No.: PCT/EP2013/064652
§ 371 (c)(1),
(2) Date: Jan. 23, 2015

(87) PCT Pub. No.: WO2014/016130
PCT Pub. Date: Jan. 30, 2014

(65) Prior Publication Data
US 2015/0203449 A1    Jul. 23, 2015

(30) Foreign Application Priority Data

Jul. 23, 2012  (FR) .................................. 12 57126

(51) Int. Cl.
| | | |
|---|---|---|
| *C07C 303/36* | (2006.01) | |
| *C07C 303/38* | (2006.01) | |
| *C07C 315/02* | (2006.01) | |
| *C07C 315/06* | (2006.01) | |
| *C07C 315/04* | (2006.01) | |
| *C07C 303/40* | (2006.01) | |
| *C07C 303/44* | (2006.01) | |
| *C07C 51/41* | (2006.01) | |
| *C07C 315/00* | (2006.01) | |

(52) U.S. Cl.
CPC ............. *C07C 303/40* (2013.01); *C07C 51/412* (2013.01); *C07C 303/36* (2013.01); *C07C 303/38* (2013.01); *C07C 303/44* (2013.01); *C07C 315/00* (2013.01); *C07C 315/04* (2013.01)

(58) Field of Classification Search
CPC .. C07C 303/36; C07C 303/38; C07C 315/02; C07C 315/06
See application file for complete search history.

(56) References Cited

U.S. PATENT DOCUMENTS

| 2,732,398 | A | 1/1956 | Brice et al. |
|---|---|---|---|
| 5,859,288 | A | 1/1999 | Forat et al. |
| 5,874,616 | A | 2/1999 | Howells et al. |
| 6,252,111 | B1 | 6/2001 | Sakai et al. |
| 2001/0021790 | A1 | 9/2001 | Yonezawa et al. |
| 2011/0269990 | A1 | 11/2011 | Honda et al. |

FOREIGN PATENT DOCUMENTS

| CN | 1319589 A | 10/2001 |
|---|---|---|
| CN | 102272096 A | 12/2011 |
| DE | 22 39 817 A1 | 2/1974 |
| EP | 0 735 023 A1 | 10/1996 |
| EP | 1 029 850 A1 | 8/2000 |
| WO | 97/23448 A1 | 7/1997 |

OTHER PUBLICATIONS

Foropoulous et al., Inorg. Chem. (1984), V.23, p. 3720-3723. The reference is not provided by the Office because it was discloed in applicants' IDS and provided by Applicants.*
Foropoulos J et al "Synthesis, Properties, and Reactions of Bis (Trifuoromethyl) Sulfonyl) Imide, (CF3S02) 2NH1", Inorganic Chemistry, American Chemical Society, Easton, US, vol. 23, No. 23, Nov. 7, 1984, pp. 3720-3723.
"Reaction of Perfluoroelkyl Sulfinate and other Oxidation Systems", Sulphination Dehalogenation Reaction and its Applications, Huang Education Press, p. 92, Apr. 2003.

* cited by examiner

*Primary Examiner* — Yong Chu

(57) ABSTRACT

The present invention relates to a method for preparing an aqueous sulfonimide compound of the formula $(Rf^1-SO_2)(Rf^2-SO_2)NH$, wherein $Rf^1$ and $Rf^2$ are independently selected from the group comprising: a fluorine atom and groups having 1 to 10 carbon atoms selected from the perfluoroalkyl, fluoroalkyl, fluoroalkenyl and fluoroallyl groups, from a mixture M1 including $(Rf^1-SO_2)(Rf^2-SO_2)NH$, $Rf^1SO_2H$ and/or $Rf^2SO_2H$, $Rf^1SO_2NH_2$ and/or $Rf^2SO_2NH_2$, characterized in that said method includes an oxidation step of said mixture M1 using an oxidizing agent in order to obtain a mixture M2 including $(Rf^1-SO_2)(Rf^2-SO_2)NH$, $Rf^1SO_3H$ and/or $Rf^2SO_3H$ and $Rf^1SO_2NH_2$ and/or $Rf^2SO_2NH_2$.

20 Claims, No Drawings

METHOD FOR PREPARING A SULFONIMIDE COMPOUND AND SALTS THEREOF

This application is a U.S. national phase entry under 35 U.S.C. §371 of International Application No. PCT/EP2013/064652, filed on Jul. 11, 2013, which claims the priority of French Application No. 1257126, filed on Jul. 23, 2012. The entire contents of these applications are being incorporated herein by reference for all purposes.

The present invention relates to a process for preparing a sulfonimide compound and salts thereof, especially lithium salts thereof.

Sulfonimide salts, such as lithium bis(trifluoromethanesulfonyl)imide (($CF_3SO_2)_2NLi$ or LiTFSI) or lithium bis(perfluoroethanesulfonyl)imide ($(C_2F_5SO_2)_2NLi$), are compounds of particular interest. They especially have properties that make them valuable compounds for electronic applications that are demanding as regards purity and quality, for example the conduction and/or the dissipation of electronic charges in the battery or antistatic markets. These properties are, on the one hand, very high acidity of the imide, and, on the other hand, an absence of complexing power of the imide with respect to the various cations. These same properties make purification operations extremely difficult and intricate. High acidity implies strong dissociation, and strong dissociation implies high solubility in polar media such as water. Furthermore, these imides often form adducts with water and, as a result, are difficult to separate from water. As a result, it is preferable for sulfonimide salts, such as $(CF_3SO_2)_2NLi$ or $((C_2F_5SO_2)_2NLi)$, to have a high purity, whether they are in anhydrous form or in aqueous solution form.

Processes for preparing sulfonimide salts exist in the prior art, especially comprising a step of purifying the sulfonimide salt by recrystallization from solvents such as dioxane. However, this purification step has several drawbacks, such as the use of a toxic, flammable solvent, the difficulty in separating the sulfonimide salt from the association complexes with dioxane, and the limited purity obtained. Furthermore, it has been observed that such processes often lead to colored salts thus having a purity that is not optimal. Moreover, there are also processes for preparing sulfonimide salts, in which the step of purification of the resulting salt consists of liquid/liquid extractions. However, in general, extractions of this type are barely purifying and involve the use of large amounts of solvent.

Moreover, the sulfonimide salts are generally prepared from sulfonimide. However, sulfonimides are typically obtained in the form of a mixture with organic impurities such as sulfinic or sulfonic acids or sulfonamides. Now, these impurities are difficult to separate from sulfonimide. As a result, the resulting sulfonimide salts do not have optimal purity.

In view of the technological importance of sulfonimide salts, and especially of $(CF_3SO_2)_2NLi$, there is a need to develop a preparation process that is easy to perform and that does not have the drawbacks mentioned above. However, in view of the absence of knowledge of the various interactions between the organic impurities as a mixture in water with sulfonimides, it is particularly difficult to develop a step for the efficient purification of said sulfonimides. There is thus a need to develop a process for preparing sulfonimides, especially $(CF_3SO_2)_2NH$, and the corresponding sulfonimide salts, especially $(CF_3SO_2)_2NLi$, in high purities.

The aim of the present invention is to provide a process for preparing sulfonimide, especially $(CF_3SO_2)_2NH$, of high purity.

Another aim of the present invention consists in providing a process for preparing a sulfonimide salt, especially $(CF_3SO_2)_2NLi$, of high purity.

Another aim of the present invention is to provide a process for preparing a sulfonimide salt, especially $(CF_3SO_2)_2NLi$, which is easy to perform.

Process for Preparing Aqueous $(Rf^1SO_2)(Rf^2SO_2)NH$

One subject of the present invention is a process for preparing an aqueous sulfonimide compound of formula $(Rf^1—SO_2)(Rf^2—SO_2)NH$, $Rf^1$ and $Rf^2$ being chosen, independently of each other, from the group consisting of: a fluorine atom and groups containing from 1 to 10 carbon atoms chosen from perfluoroalkyl, fluoroalkyl, fluoroalkenyl, fluoroaryl and fluoroallyl groups, starting with a mixture M1 comprising $(Rf^1—SO_2)(Rf^2—SO_2)NH$, $Rf^1SO_2H$ and/or $Rf^2SO_2H$, $Rf^1SO_2NH_2$ and/or $Rf^2SO_2NH_2$, and characterized in that it comprises a step of oxidizing said mixture M1 with an oxidizing agent, to obtain a mixture M2 comprising $(Rf^1—SO_2)(Rf^2—SO_2)NH$, $Rf^1SO_3H$ and/or $Rf^2SO_3H$, and $Rf^1SO_2NH_2$ and/or $Rf^2SO_2NH_2$.

According to the invention, $Rf^1$ and $Rf^2$ may be identical or different.

According to one embodiment, $Rf^1$ and $Rf^2$ are chosen, independently of each other, from the group consisting of: a fluorine atom and groups containing from 1 to 10 carbon atoms, chosen from perfluoroalkyl, fluoroalkyl, fluoroalkenyl and fluoroallyl groups.

This oxidation step makes it possible, surprisingly, to selectively oxidize $Rf^1SO_2H$ and/or $Rf^2SO_2H$ into $Rf^1SO_3H$ and/or $Rf^2SO_3H$.

According to the invention, the mixture M2 may be advantageously subjected to a distillation step in aqueous medium to separate $(Rf^1—SO_2)(Rf^2—SO_2)NH$ from $Rf^1SO_3H$ and/or from $Rf^2SO_3H$, and from $Rf^1SO_2NH_2$ and/or $Rf^2SO_2NH_2$. Thus, the purity of the $(Rf^1—SO_2)(Rf^2—SO_2)NH$ obtained is high.

According to one embodiment, the process for preparing an aqueous sulfonimide compound of formula $(Rf^1—SO_2)(Rf^2—SO_2)NH$, $Rf^1$ and $Rf^2$ being as defined above, from a mixture M1 comprising $(Rf^1—SO_2)(Rf^2—SO_2)NH$, $Rf^1SO_2H$ and/or $Rf^2SO_2H$, $Rf^1SO_2NH_2$ and/or $Rf^2SO_2NH_2$, comprises:

i) a step of oxidizing said mixture M1 with an oxidizing agent, to obtain a mixture M2 comprising $(Rf^1—SO_2)(Rf^2—SO_2)NH$, $Rf^1SO_3H$ and/or $Rf^2SO_3H$, and $Rf^1SO_2NH_2$ and/or $Rf^2SO_2NH_2$; and ii) a step of distilling the mixture M2, in aqueous medium, to separate $(Rf^1—SO_2)(Rf^2—SO_2)NH$ from $Rf^1SO_3H$ and/or from $Rf^2SO_3H$, and from $Rf^1SO_2NH_2$ and/or $Rf^2SO_2NH_2$.

A subject of the present invention is also a process for preparing an aqueous sulfonimide compound of formula $(Rf^1SO_2)(Rf^2SO_2)NH$, $Rf^1$ and $Rf^2$ being as defined above, from a mixture M1 comprising $(Rf^1SO_2)(Rf^2SO_2)NH$ and $Rf^1SO_2H$ and/or $Rf^2SO_2H$, characterized in that it comprises:

i) a step of oxidizing said mixture M1 with an oxidizing agent, to obtain a mixture M2 comprising $(Rf^1SO_2)(Rf^2SO_2)NH$ and $Rf^1SO_3H$ and/or $Rf^2SO_3H$; and ii) a step of distilling the mixture M2, in aqueous medium, to separate $(Rf^1SO_2)(Rf^2SO_2)NH$ from $Rf^1SO_3H$ and/or from $Rf^2SO_3H$.

In accordance with the invention, the sulfonimide compound of formula $(Rf^1SO_2)(Rf^2SO_2)NH$ obtained after the implementation of the process according to the invention is present in aqueous solution.

According to one embodiment, when $Rf^1$ and $Rf^2$ are identical, the sulfonimide compound $(Rf^1SO_2)(Rf^2SO_2)NH$ synthesized is a "symmetrical" sulfonimide. Preferably, said symmetrical sulfonimide is chosen from the group consisting of: $(CF_3SO_2)_2NH$, $(CHF_2SO_2)_2NH$, $(CH_2FSO_2)_2NH$, $(C_2F_5SO_2)_2NH$, $(C_3F_7SO_2)_2NH$, $F(SO_2)_2NH$ and $(C_4F_9SO_2)_2NH$.

According to one embodiment, when $Rf^1$ and $Rf^2$ are different, the sulfonimide compound $(Rf^1SO_2)(Rf^2SO_2)NH$ synthesized is chosen from the group consisting of: $(FSO_2)(CF_3SO_2)NH$, $(FSO_2)(C_2F_5SO_2)NH$, $(FSO_2)(C_3F_7SO_2)NH$, $(FSO_2)(C_4F_9SO_2)NH$, $(CF_3SO_2)(C_2F_5SO_2)NH$, $(CF_3SO_2)(C_3F_7SO_2)NH$, $(CF_3SO_2)(C_4F_9SO_2)NH$, $(C_2F_5SO_2)(C_3F_7SO_2)NH$, $(C_2F_5SO_2)(C_4F_9SO_2)NH$ and $(C_3F_7SO_2)(C_4F_9SO_2)NH$.

In the context of the invention, and unless otherwise mentioned, when $Rf^1$ and $Rf^2$ are identical, the sulfonimide (or salts thereof) obtained is a symmetrical sulfonimide (or salts thereof).

In the context of the invention, and unless otherwise mentioned, when $Rf^1$ and $Rf^2$ are different, the sulfonimide (or salts thereof) obtained is a dissymmetrical sulfonimide (or salts thereof).

According to one embodiment, $Rf^1$ and $Rf^2$ are identical.

According to one embodiment, $Rf^1$ and $Rf^2$ are perfluoroalkyl groups comprising from 1 to 10 carbon atoms, preferably from 1 to 4 and even more preferentially from 1 to 2 carbon atoms.

According to one embodiment, $Rf^1$ and $Rf^2$ represent $CF_3$. In this case, the abovementioned process makes it possible to prepare aqueous $(CF_3SO_2)_2NH$, i.e. an aqueous solution of $(CF_3SO_2)_2NH$.

According to another embodiment, $Rf^1$ and $Rf^2$ represent $C_2F_5$. In this case, the abovementioned process makes it possible to prepare aqueous $(C_2F_5SO_2)_2NH$, i.e. an aqueous solution of $(C_2F_5SO_2)_2NH$.

According to one embodiment, the compounds $Rf^1SO_2H$ and $Rf^2SO_2H$ are chosen, independently of each other, from the group consisting of: $CHF_2SO_2H$, $CH_2FSO_2H$, $CF_3SO_2H$, $C_2F_5SO_2H$, $C_3F_7SO_2H$, $FSO_2H$ and $C_4F_9SO_2H$.

According to one embodiment, the compounds $Rf^1SO_3H$ and $Rf^2SO_3H$ are chosen, independently of each other, from the group consisting of: $CHF_2SO_2H$, $CH_2FSO_2H$, $CF_3SO_3H$, $C_2F_5SO_3H$, $C_3F_7SO_3H$, $FSO_3H$ and $C_4F_9SO_3H$.

In the context of the invention, and unless otherwise mentioned, the term "aqueous $(Rf^1SO_2)(Rf^2SO_2)NH$" means an aqueous solution of $(Rf^1SO_2)(Rf^2SO_2)NH$.

According to one embodiment, $Rf^1SO_2H$ and/or $Rf^2SO_2H$ and especially $CF_3SO_2H$ is a minor product in the mixture M1, and $(Rf^1SO_2)(Rf^2SO_2)NH$ and especially $(CF_3SO_2)_2NH$ is a major product in said mixture.

In the context of the invention, and unless otherwise mentioned, the term "minor product in a mixture" means a product constituting not more than 20% by weight of said mixture, preferably not more than 10%, preferably not more than 5%, relative to the other constituents of said mixture.

In the context of the invention, and unless otherwise mentioned, the term "major product in a mixture" means a product constituting at least 30% by weight of said mixture, preferably at least 50%, relative to the other constituents of said mixture.

According to one embodiment, the mixture M1 comprises from 0.01% to 5% and preferably from 0.1% to 2% by weight of $Rf^1SO_2H$ and/or $Rf^2SO_2H$.

According to one embodiment, the mixture M1 comprises from 30% to 95% by weight of $(Rf^1SO_2)(Rf^2SO_2)NH$ and especially $(CF_3SO_2)_2NH$, preferably from 50% to 95% and preferentially from 60% to 95% by weight.

According to the invention, the mixture M1 may also comprise other compounds, chosen especially from $Rf^1SO_2NH_2$, $Rf^2SO_2NH_2$, $Rf^1SO_3H$, $Rf^2SO_3H$, HF, HBr and HCl. In particular, these compounds are minor side products in the mixture M1. According to the invention, they are also referred to as organic and mineral impurities.

According to one embodiment, the compounds $Rf^1SO_2NH_2$ and $Rf^2SO_2NH_2$ are chosen, independently of each other, from the group consisting of: $CHF_2SO_2NH_2$, $CH_2FSO_2NH_2$, $CF_3SO_2NH_2$, $C_2F_5SO_2NH_2$, $C_3F_7SO_2NH_2$ and $C_4F_9SO_2NH_2$. In particular, $Rf^1SO_2NH_2$ and/or $Rf^2SO_2NH_2$ represent(s) $CF_3SO_2NH_2$.

According to one embodiment, the mixture M1 comprises $(Rf^1SO_2)(Rf^2SO_2)NH$ and especially $(CF_3SO_2)_2NH$, and organic and mineral impurities such as $Rf^1SO_2H$, $Rf^2SO_2H$, $Rf^1SO_2NH_2$, $Rf^2SO_2NH_2$, $Rf^1SO_3H$, $Rf^2SO_3H$, HF, HBr or HCl. In particular, M1 comprises $(CF_3SO_2)_2NH$ and organic and mineral impurities chosen from the group consisting of: $CF_3SO_2H$, $CF_3SO_2NH_2$, $CF_3SO_3H$, HF, HBr and HCl.

According to one embodiment, the mixture M1 comprises from 0.01% to 5% and preferably from 0.1% to 2% by weight of $Rf^1SO_2NH_2$ and/or $Rf^2SO_2NH_2$.

In the process according to the invention, the oxidizing agent of the oxidation step i) may be chosen from the group consisting of: hydrogen peroxide, organic hydroperoxides and peroxides, bleach, sodium persulfate, sodium perborate, Oxone, ozone and nitrous oxide. In particular, the oxidizing agent is hydrogen peroxide ($H_2O_2$), especially $H_2O_2$ at 30% by weight.

According to one embodiment, the oxidation step i) is performed at a temperature ranging from 20° C. to 100° C., preferably from 50° C. to 90° C. and preferentially from 75° C. to 85° C. In particular, the oxidation step i) is performed at 80° C.

According to one embodiment, the oxidation step i) is performed for from 5 to 120 minutes, preferably from 10 to 60 minutes and preferentially from 20 to 40 minutes.

According to the invention, the mixture M2 may also comprise other compounds, chosen especially from $Rf^1SO_2NH_2$, $Rf^2SO_2NH_2$, $Rf^1SO_3H$, $Rf^2SO_3H$, HF, HBr and HCl. In particular, these compounds are minor side products in the mixture M2. According to the invention, they are also referred to as organic and mineral impurities.

According to one embodiment, the mixture M2 comprises $(Rf^1SO_2)(Rf^2SO_2)NH$ and organic and mineral impurities such as $Rf^1SO_2NH_2$, $Rf^2SO_2NH_2$, $Rf^1SO_3H$, $Rf^2SO_3H$, HF, HBr and HCl. In particular, M2 comprises $(CF_3SO_2)_2NH$ and organic and mineral impurities such as $CF_3SO_2NH_7$, $CF_3SO_3H$, HF, HBr and HCl.

According to one embodiment, the mixture M2 does not comprise any $Rf^1SO_2H$ and/or $Rf^2SO_2H$, such as $CF_3SO_2H$, or only very small amounts, i.e. less than 200 ppm, preferably less than 50 ppm and preferably less than 10 ppm.

According to one embodiment, the mixture M2 comprises from 0.01% to 5% and preferably from 0.1% to 2% by weight of $Rf^1SO_2NH_2$ and/or $Rf^2SO_2NH_2$.

It has been shown that the oxidation step of the mixture M1 advantageously makes it possible to oxidize $Rf^1SO_2H$ and/or $Rf^2SO_2H$ present in the mixture M1 into $Rf^1SO_3H$ and/or $Rf^2SO_3H$. In particular, the oxidation step i) is a selective oxidation of $Rf^1SO_2H$ and/or $Rf^2SO_2H$ relative to $(Rf^1SO_2)(Rf^2SO_2)NH$ and relative to $Rf^1SO_2NH_2$ and/or $Rf^2SO_2NH_2$. Specifically, surprisingly, $Rf^1SO_2NH_2$ and/or $Rf^2SO_2NH_2$ was not oxidized during the oxidation step i).

In the context of the invention, the term "selective oxidation of one compound relative to another" means the action of an oxidizing agent on one specific compound without affecting the other compound. Mention may especially be made of the selective oxidation of $Rf^1SO_2H$ and/or $Rf^2SO_2H$ present in the mixture M1 into $Rf^1SO_3H$ and/or $Rf^2SO_3H$, without $(Rf^1SO_2)(Rf^2SO_2)NH$, and $Rf^1SO_2NH_2$ and/or $Rf^2SO_2NH_2$ being oxidized. In particular, mention may be made of the selective oxidation of $CF_3SO_2H$ present in the mixture M1 into $CF_3SO_3H$ without $(CF_3SO_2)_2NH$ and $CF_3SO_2NH_2$ being oxidized.

The distillation step ii) of the mixture M2 is performed in aqueous medium, to give an aqueous solution of $(Rf^1SO_2)(Rf^2SO_2)NH$, and especially an aqueous solution of $(CF_3SO_2)_2NH$.

According to the invention, the distillation step ii) may be performed in the presence of an amount of water sufficient to perform the distillation of $(Rf^1SO_2)(Rf^2SO_2)NH$. In particular, the water of the aqueous medium of step ii) was added after the oxidation step i). In particular, the water of the aqueous medium of step ii) also originates from the prior oxidation step, and especially from the hydrogen peroxide at 30% by weight.

According to one embodiment, an aqueous solution comprising from 40% to 95% by weight, preferably from 60% to 80% by weight and preferentially 65% to 75% by weight of $(Rf^1SO_2)(Rf^2SO_2)NH$ is obtained after the oxidation step i).

According to the invention, the distillation step may be performed in distillation apparatus comprising a boiler and a distillation column.

According to one embodiment, the distillation step is performed at a temperature in the boiler ranging from 50° C. to 300° C., preferably from 50° C. to 200° C. and preferentially from 80° C. to 150° C. In particular, the temperature in the boiler ranges from 80° C. to 130° C. The distillation step may be performed, for example, at a temperature in the boiler of from 110° C. to 130° C.

In the context of the invention, and unless otherwise mentioned, the temperature in the boiler corresponds to the temperature at the bottom of the distillation column.

According to one embodiment, the distillation step is performed in distillation apparatus comprising a distillation column in which the temperature at the top of the column ranges from 20° C. to 180° C., preferably from 40° C. to 150° C. and preferentially from 40° C. to 130° C. In particular, the temperature at the top of the distillation column ranges from 40° C. to 100° C. In particular, the temperature at the top of the column ranges from 50° C. to 80° C.

According to one embodiment, the distillation step ii) is performed at atmospheric pressure in the distillation column. According to another embodiment, the step of distilling the mixture M2 is performed under vacuum, especially at a pressure in the column ranging from 1 to 1000 mbar (0.1 to 100 kPa), preferably from 5 to 500 mbar (0.5 to 50 kPa) and preferentially from 5 to 200 mbar (0.5 to 20 kPa). In particular, the pressure in the column ranges from 5 to 100 mbar and preferably from 5 to 60 mbar. In particular, the pressure ranges from 20 mbar to 60 mbar.

According to one embodiment, the distillation step comprises the recovery of various distillation fractions, said fractions being recovered under various distillation conditions, namely various temperatures in the boiler and at the top of the column and various pressures.

Thus, according to a particular embodiment, a first fraction is collected under the following conditions: the distillation step is performed at a temperature in the boiler of between 70° C. and 130° C., at a column pressure ranging from 20 to 60 mbar and at a temperature at the top of the column ranging from 40° C. to 100° C.

Next, according to another particular embodiment, a second fraction is collected under the following conditions: the distillation step is performed at a temperature at the top of the column ranging from 50° C. to 80° C., at a column pressure ranging from 5 to 15 mbar and at a temperature in the boiler ranging from 90° C. to 130° C.

According to the invention, the distillation column can be adapted to the desired degree of purity, and it can consist of materials suitable for the acidic conditions of the mixture to be distilled.

According to the invention, the distillation apparatus comprising a boiler and a distillation column may consist of materials suitable for the acidic conditions of the mixture to be distilled. In particular, the distillation apparatus is chosen from the following materials: glass, Teflon, graphite.

According to the invention, the distillation step may be performed using a column comprising a number of theoretical plates that is suitable for enabling the distillation of $(Rf^1SO_2)(Rf^2SO_2)NH$ in water.

According to one embodiment, the distillation is performed using a distillation column comprising from 2 to 40 theoretical plates, preferably from 4 to 20 and preferentially from 5 to 15. In particular, the distillation is performed using a column comprising from 7 to 14 theoretical plates.

In the context of the invention, and unless otherwise mentioned, the term "theoretical plates" means ideal plates in which the heat losses are zero and the thermodynamic equilibria are instantaneous.

According to one embodiment, the distillation step ii) is performed at a reflux rate ranging from 1 to 50, preferably from 1 to 40 and preferentially from 5 to 30. In particular, the reflux rate ranges from 5 to 15.

In the context of the invention, and unless otherwise mentioned, the term "reflux rate" means the ratio between the molar rate (by mass or volume) of reflux (fractions of condensed vapors returned at the top of the column) and the molar rate (by mass or volume, respectively) of pure distillate recovered.

According to the process of the invention, the distillation step ii) may be performed continuously or batchwise.

According to one embodiment, the step of distilling the mixture M2 makes it possible to collect different fractions according to the products contained in the mixture M2. Part of the organic impurities contained in the mixture M2 remains at the bottom of the column, such as $Rf^1SO_2NH_2$ and/or $Rf^2SO_2NH_2$ and the hydrate of $Rf^1SO_3H$ and/or of $Rf^2SO_3H$. Thus, after the process, an aqueous solution of $(Rf^1SO_2)(Rf^2SO_2)NH$ of high purity is recovered, especially free of $Rf^1SO_2H$ and/or $Rf^2SO_2H$, of $Rf^1SO_3H$ and/or $Rf^2SO_3H$, and of $Rf^1SO_2NH_2$ and/or $Rf^2SO_2NH_2$.

According to the invention, the process may comprise a step of recycling $Rf^1SO_2NH_2$ and/or $Rf^2SO_2NH_2$.

According to one embodiment, after the distillation step ii), $Rf^1SO_2NH_2$ and/or $Rf^2SO_2NH_2$ is/are subjected to various steps of neutralization and extraction of the distillation residue. After these steps, pure $Rf^1SO_2NH_2$ and/or $Rf^2SO_2NH_2$ are recovered.

According to one embodiment, pure $Rf^1SO_2NH_2$ and/or $Rf^2SO_2NH_2$ is/are recycled into the process of the invention, and especially into the ammonolysis step described hereinbelow.

In the context of the invention, and unless otherwise mentioned, the term "product of high purity" means a product with a purity of greater than 95%, preferably greater than 99% and preferentially greater than or equal to 99.5%.

According to one embodiment, an aqueous solution comprising from 40% to 95% by weight, preferably from 60% to 80% by weight and preferentially 65% to 75% by weight of $(Rf^1SO_2)(Rf^2SO_2)NH$ is obtained after the oxidation and distillation steps.

It was thus discovered that the oxidation step i), followed by a distillation step ii), of the mixture M1 especially comprising $(Rf^1SO_2)(Rf^2SO_2)NH$ and organic impurities such as $Rf^1SO_2H$ and/or $Rf^2SO_2H$, $Rf^1SO_3H$ and/or $Rf^2SO_3H$, and $Rf^1SO_2NH_2$ and/or $Rf^2SO_2NH_2$, makes it possible to purify $(Rf^1SO_2)(Rf^2SO_2)NH$.

$Rf^1SO_2H$ and/or $Rf^2SO_2H$ contained in the mixture M1 especially has/have a boiling point very close to that of $(Rf^1SO_2)(Rf^2SO_2)NH$ (for example $CF_3SO_2H$ has a boiling point of 165° C., $CF_3SO_2NH_2$ has a boiling point of 164° C. and $(CF_3SO_2)_2NH$ has a boiling point of 167° C.). Furthermore, $Rf^1SO_2H$ and/or $Rf^2SO_2H$ do(es) not form hydrates with water. Finally, the sulfonamide derivatives $Rf^1SO_2NH_2$ and/or $Rf^2SO_2NH_2$ are impurities typically present in the processes for preparing sulfonimides and salts thereof, which are difficult to separate from said sulfonimides.

Thus, these various factors as a whole are such that the purification of $(Rf^1SO_2)(Rf^2SO_2)NH$ is difficult.

The oxidation step according to the invention especially makes it possible to selectively oxidize $Rf^1SO_2H$ and/or $Rf^2SO_2H$ into $Rf^1SO_3H$ and/or $Rf^2SO_3H$, which may then be advantageously separated from $(Rf^1SO_2)(Rf^2SO_2)NH$ during the distillation step.

Surprisingly, this oxidation step does not make it possible to remove the impurities of sulfonamide type $Rf^1SO_2NH_2$ and/or $Rf^2SO_2NH_2$, which are not oxidized.

The combination of various specific distillation parameters, such as the reflux rate, the number of theoretical plates, the boiler temperature, the temperature at the top of the column and the distillation column pressure, allows particularly efficient separation of the sulfonamide impurities $Rf^1SO_2NH_2$ and/or $Rf^2SO_2NH_2$ from the product $(Rf^1SO_2)(Rf^2SO_2)NH$. Thus, an aqueous solution of $(Rf^1SO_2)(Rf^2SO_2)NH$ of very high purity is advantageously obtained.

Moreover, it has been shown that the sulfonamide impurities $Rf^1SO_2NH_2$ and/or $Rf^2SO_2NH_2$ may advantageously be recycled and reused in the process of the invention, for example during the introduction of sulfonamides as reagents. This thus results in a process advantageously comprising a step of upgrading the sulfonamide impurities $Rf^1SO_2NH_2$ and/or $Rf^2SO_2NH_2$, at least by recycling within the process. This recycling is particularly advantageous from an industrial viewpoint.

Preliminary Distillation Step

According to the invention, the process for preparing aqueous $(Rf^1SO_2)(Rf^2SO_2)NH$ may comprise a preliminary step of distilling a mixture M'1, comprising $(Rf^1SO_2)(Rf^2SO_2)NH$ and $Rf^1SO_2H$ and/or $Rf^2SO_2H$, leading to the mixture M1. Typically, this distillation step leading to the mixture M1 is a distillation for grossly purifying the mixture M'1. In particular, the process for preparing aqueous $(CF_3SO_2)_2NH$ comprises a preliminary step of distilling a mixture M'1, comprising $(CF_3SO_2)_2NH$ and $CF_3SO_2H$, leading to the mixture M1.

According to one embodiment, the distillation of the mixture M'1 may make it possible to separate certain impurities, such as the tertiary amine hydrogen sulfates $NR'_3$, $R'_3$ representing a linear or branched alkyl group containing from 1 to 20 carbon atoms, from $(Rf^1SO_2)(Rf^2SO_2)NH$. In particular, the tertiary amine hydrogen sulfates are triethylamine or diisopropylethylamine hydrogen sulfates. Thus, the mixture M1 corresponds to the mixture M'1 especially free of tertiary amine hydrogen sulfate $NR'_3$.

Thus, the present invention relates to a process for preparing aqueous $(Rf^1SO_2)(Rf^2SO_2)NH$ from a mixture M'1 comprising $(Rf^1SO_2)(Rf^2SO_2)NH$ and $Rf^1SO_2H$ and/or $Rf^2SO_2H$, characterized in that it comprises:
 a step of distilling said mixture M'1, to give a mixture M1;
 a step of oxidizing said mixture M1 with an oxidizing agent, to obtain a mixture M2 comprising $(Rf^1SO_2)(Rf^2SO_2)NH$ and $Rf^1SO_3H$ and/or $Rf^2SO_3H$; and
 a step of distilling the mixture M2, in aqueous medium, enabling separation of $(Rf^1SO_2)(Rf^2SO_2)NH$ and $Rf^1SO_3H$ and/or $Rf^2SO_3H$.

Other Preliminary Steps

According to one embodiment, the sulfonimide $(Rf^1SO_2)(Rf^2SO_2)NH$ present in the abovementioned mixture M'1 is obtained via a step of acidification of an organic phase comprising a complex $(Rf^1SO_2)(Rf^2SO_2)NH,NR'_3$, R' representing a linear or branched alkyl group containing from 1 to 20 carbon atoms. Preferably, the complex $(Rf^1SO_2)(Rf^2SO_2)NH,NR'_3$ is $(Rf^1SO_2)(Rf^2SO_2)NH,NEt_3$, in which Et represents an ethyl radical $C_2H_5$, or $(Rf^1SO_2)(Rf^2SO_2)NH,NEt(i-Pr)_2$, in which i-Pr represents an isopropyl radical. Even more preferentially, the complex $(Rf^1SO_2)(Rf^2SO_2)NH,NR'_3$ is $(CF_3SO_2)_2NH,NEt_3$ or $(CF_3SO_2)_2NH,NEt(i-Pr)_2$.

According to one embodiment, the abovementioned complex $(Rf^1SO_2)(Rf^2SO_2)NH,NR'_3$ is obtained via a step of ammonolysis of $Rf^1SO_2X$ and of $Rf^2SO_2X$, X representing Cl, Br or F, $Rf^1$ and $Rf^2$ possibly being identical or different.

According to another embodiment, the abovementioned complex $(Rf^1SO_2)(Rf^2SO_2)NH,NR'_3$ is obtained via a step of ammonolysis of $Rf^1SO_2X$ in the presence of $Rf^2SO_2NH_2$, X representing Cl, Br or F, $Rf^1$ and $Rf^2$ possibly being identical or different.

According to one embodiment, $Rf^1SO_2X$ is obtained via a step of oxidation of a mixture M3 comprising $Rf^1CO_2M^a$, $M^a$ representing an alkali metal, and $Rf^1SO_2M^a$, to obtain a two-phase mixture M4, said mixture M4 comprising $Rf^1SO_2X$ and $Rf^1CO_2M^a$.

According to the invention, $M^a$ represents an alkali metal chosen especially from: K, Li, Na, Cs.

According to another embodiment, $Rf^1SO_2X$, with X=F, is obtained by electrofluorination of $R^hSO_2F$, $R^h$ representing a hydrocarbon-based chain identical to that of $Rf^1$, said chain comprising hydrogen atoms in place of the fluorine atoms, and $R^hSO_2F$ optionally being obtained from $R^hSO_2W$, with W=Cl, Br or I.

Preferably, W represents Cl.

According to one embodiment, the mixture M3 is obtained by:
 a step of sulfination of $Rf^1CO_2M^a$, especially of $CF_3CO_2K$, in an organic solvent, to give a mixture M comprising $Rf^1SO_2M^a$, especially $CF_3SO_2K$, and said organic solvent; and then
 a step of distillation of said organic solvent from the mixture M, to obtain the mixture M without said solvent; and then
 a step of separation of the salts, and especially a step of liquid/liquid extraction, of the mixture M derived from the distillation step.

According to one embodiment, $Rf^1CO_2M^a$ is obtained via a step of salification of $Rf^1CO_2H$, preferably of $CF_3CO_2H$.

Advantageously, at least for the sulfination step, $M^a$ is potassium.

These various steps are more precisely detailed in the description hereinbelow.

Process for Preparing the Sulfonimide Salt $(Rf^1SO_2)(Rf^2SO_2)NM^b$

A subject of the present invention is also the preparation of $(Rf^1SO_2)(Rf^2SO_2)NM^b$, $M^b$ representing an alkali metal, chosen especially from: K, Li, Na and Cs, starting with the process for preparing $(Rf^1SO_2)(Rf^2SO_2)NH$ as described above.

A subject of the present invention is also a process for preparing $(Rf^1SO_2)(Rf^2SO_2)NM^b$, preferably $(Rf^1SO_2)(Rf^2SO_2)NLi$, starting with aqueous $(Rf^1SO_2)(Rf^2SO_2)NH$, said process comprising the preparation of aqueous $(Rf^1SO_2)(Rf^2SO_2)NH$ according to the process as described above.

According to one embodiment, $M^b$ represents Li. Thus, the process for preparing $(Rf^1SO_2)(Rf^2SO_2)NM^b$ corresponds to the process for preparing $(Rf^1SO_2)(Rf^2SO_2)NLi$.

According to one embodiment, when $Rf^1$ and $Rf^2$ are identical, the resulting sulfonimide salt is said to be symmetrical, and is especially chosen from: $(CF_3SO_2)_2NM^b$, $(CHF_2SO_2)_2NM^b$, $(CH_2FSO_2)_2NM^b$ $(C_2F_5SO_2)_2NM^b$, $(C_3F_7SO_2)_2NM^b$, $(FSO_2)_2NM^b$, $(C_4F_9SO_2)_2NM^b$. In particular, the sulfonimide salts are $(FSO_2)_2NLi$ ($Rf^1=Rf^2=F$) or $(CF_3SO_2)_2NLi$ ($Rf^1=Rf^2=CF_3$) or $(C_2F_5SO_2)_2NLi$ ($Rf^1=Rf^2=C_2F_5$), and preferably $(CF_3SO_2)_2NLi$ and $(C_2F_5SO_2)_2NLi$.

According to one embodiment, when $Rf^1$ and $Rf^2$ are different, the resulting sulfonimide salt is said to be dissymmetrical, and is especially chosen from: $(FSO_2)(CF_3SO_2)NM^b$, $(FSO_2)(C_2F_5SO_2)NM^b$, $(FSO_2)(C_3F_7SO_2)NM^b$, $(FSO_2)(C_4F_9SO_2)NM^b$, $(CF_3SO_2)(C_2F_5SO_2)NM^b$, $(CF_3SO_2)(C_3F_7SO_2)NM^b$, $(CF_3SO_2)(C_4F_9SO_2)NM^b$, $(C_2F_5SO_2)(C_3F_7SO_2)NM^b$, $(C_2F_5SO_2)(C_4F_9SO_2)NM^b$, $(C_3F_7SO_2)(C_4F_9SO_2)NM^b$.

According to one embodiment, $Rf^1$ and $Rf^2$, which may be identical or different, are perfluoroalkyls.

According to one embodiment, $(Rf^1SO_2)(Rf^2SO_2)NM^b$ is chosen from $(CF_3SO_2)_2NLi$ and $(C_2F_5SO_2)_2NLi$. Preferably, $(Rf^1SO_2)(Rf^2SO_2)NM^b$ is $(CF_3SO_2)_2NLi$.

According to one embodiment, the process for preparing $(Rf^1SO_2)(Rf^2SO_2)NM^b$ comprises the preparation of aqueous $(Rf^1SO_2)(Rf^2SO_2)NH$ from a mixture M1 comprising $(Rf^1SO_2)(Rf^2SO_2)NH$ and $Rf^1SO_3H$ and/or $Rf^2SO_3H$ according to the process as described above and characterized in that it comprises:
 i) a step of oxidizing said mixture M1 with an oxidizing agent, to obtain a mixture M2 comprising $(Rf^1SO_2)(Rf^2SO_2)NH$ and $Rf^1SO_3H$ and/or $Rf^2SO_3H$; and
 ii) a step of distilling the mixture M2, in aqueous medium, to separate $(Rf^1SO_2)(Rf^2SO_2)NH$ from $Rf^1SO_3H$ and/or from $Rf^2SO_3H$.

According to one embodiment, the process for preparing $(Rf^1SO_2)(Rf^2SO_2)NM^b$ and especially $(Rf^1SO_2)(Rf^2SO_2)NLi$ comprises a step of neutralization of aqueous $(Rf^1—SO_2)(Rf^2—SO_2)NH$ as obtained according to the process described above, in the presence of an alkali metal base, and especially a lithiated base, where appropriate followed by a drying step.

A subject of the present invention is also a process for preparing $(Rf^1SO_2)(Rf^2SO_2)NM^b$, preferably $(CF_3SO_2)_2NLi$, comprising the following steps:
 a step a) of salification of $Rf^1CO_2H$ to $Rf^1CO_2M^a$;
 a step b) of sulfination of $Rf^1CO_2M^a$ to $Rf^1SO_2M^a$;
 a step c) of oxidation of $Rf^1SO_2M^a$ to $Rf^1SO_2X$;
 a step d) of ammonolysis of $Rf^1SO_2X$ to $(Rf^1SO_2)(Rf^2—SO_2)NH,NR'_3$;
 a step e) of acidification of $(Rf^1SO_2)(Rf^2SO_2)NH,NR'_3$ to $(Rf^1SO_2)(Rf^2SO_2)NH$;
 a step g) of neutralization, with an alkali metal base, of $(Rf^1SO_2)(Rf^2SO_2)NH$ to $(Rf^1—SO_2)(Rf^2—SO_2)NM^b$; and
 where appropriate, a step h) of drying of $(Rf^1SO_2)(Rf^2SO_2)NM^b$,
in which $(Rf^1—SO_2)(Rf^2—SO_2)NH$, obtained after step e), is in the form of a mixture, said mixture having been subjected, before step g), to an oxidation step i) and a distillation step ii) as described previously, $Rf^1$, $Rf^2$, $M^a$ and $M^b$ being as defined above.

According to a particular embodiment, the present invention relates to a process for preparing $(CF_3SO_2)_2NLi$, comprising the following steps:
 a step a) of salification of $CF_3CO_2H$ to $CF_3CO_2K$;
 a step b) of sulfination of $CF_3CO_2K$ to $CF_3SO_2K$;
 a step c) of oxidation of $CF_3SO_2K$ to $CF_3SO_2X$;
 a step d) of ammonolysis of $CF_3SO_2X$ to $(CF_3SO_2)_2NH$, $NR'_3$;
 a step e) of acidification of $(CF_3SO_2)_2NH,NR'_3$ to $(CF_3SO_2)_2NH$;
 a step g) of neutralization, with a lithiated base, of $(CF_3SO_2)_2NH$ to $(CF_3SO_2)_2NHLi$; and
 where appropriate, a step h) of drying of $(CF_3SO_2)_2NHLi$,
in which $(CF_3SO_2)_2NH$, obtained after step e), is in the form of a mixture comprising $(CF_3SO_2)_2NH$ and $CF_3SO_2H$, said mixture having been subjected, before step g), to an oxidation step i) and a distillation step ii) as described previously.

A subject of the present invention is also a process for preparing $(Rf^1—SO_2)(Rf^2—SO_2)NM^b$, comprising the following steps:
 a step b') of converting $R^hSO_2W$, with W representing Cl, Br or I, into $R^hSO_2F$;
 a step c') of electrofluorination of $R^hSO_2F$ to $Rf^1SO_2F$;
 a step d) of ammonolysis of $Rf^1SO_2F$ to $(Rf^1SO_2)(Rf^2—SO_2)NH,NR'_3$;
 a step e) of acidification of $(Rf^1SO_2)(Rf^2SO_2)NH,NR'_3$ to $(Rf^1SO_2)(Rf^2SO_2)NH$;
 a step g) of neutralization, with an alkali metal base, of $(Rf^1SO_2)(Rf^2SO_2)NH$ to $(Rf^1—SO_2)(Rf^2—SO_2)NM^b$; and
 where appropriate, a step h) of drying of $(Rf^1SO_2)(Rf^2SO_2)NM^b$,
in which $(Rf^1—SO_2)(Rf^2—SO_2)NH$, obtained after step e), is in the form of a mixture, said mixture having been subjected, before step g), to an oxidation step i) and to a distillation step ii) as defined previously, and $Rf^1$, $R^h$, $Rf^2$, $M^b$ being as defined above.

According to the invention, the various steps of the process mentioned above, and detailed below, and especially the sulfination, oxidation and ammonolysis steps, may be performed in a continuous or batch reactor.

According to the invention, the various reactions may be performed in a piston-flow reactor, for example a single tubular reactor, or a cascade of perfectly stirred reactors.

In the context of the invention, and unless otherwise mentioned, the term "tubular reactor" means a tube-shaped reactor.

In the context of the invention, and unless otherwise mentioned, the term "piston-flow reactor" means a reactor in which the flow is unidirectional, and in which, in a plane perpendicular to the flow, all the fluid streams move at a uniform speed. In such a flow, the radial mixing is perfect, whereas there is no axial mixing.

The various steps are detailed below.

Salification Step a)

In the context of the invention, the process for preparing $(Rf^1SO_2)(Rf^2SO_2)NM^b$ may comprise a step a) of salification of $Rf^1CO_2H$ to $Rf^1CO_2M^a$.

The step of salification of $Rf^1CO_2H$ to $Rf^1CO_2M^a$ may be performed according to the processes known to those skilled in the art.

According to one embodiment, $M^a$ is chosen from the group consisting of: K, Li, Na, Cs. Preferably, $M^a$ represents K.

According to one embodiment, $Rf^1CO_2H$ is $CF_3CO_2H$.

According to one embodiment, $Rf^1CO_2K$ is $CF_3CO_2K$.

In the context of the invention, and unless otherwise mentioned, the term "salification" means the reaction directed toward preparing the alkali metal salt $Rf^1CO_2M^a$ from the acid $Rf^1CO_2H$. Mention may be made, for example, of the salification of trifluoroacetic acid $CF_3CO_2H$ to potassium trifluoroacetate $CF_3CO_2K$ or the salification of $C_2F_5CO_2H$ to $C_2F_5CO_2K$.

According to one embodiment, the step of salification a) of $Rf^1CO_2H$ to $Rf^1CO_2M^a$ consists of the slow addition of $Rf^1CO_2H$ to an aqueous alkaline solution and especially an aqueous potassium hydroxide solution. The addition is especially performed for a time sufficient for the temperature of the reaction medium to remain between 30° C. and 80° C.

After the salification step a), a solution of $Rf^1CO_2M^a$, preferably $Rf^1CO_2K$ and preferentially of potassium trifluoroacetate in water may be obtained.

According to one embodiment, a step of concentrating the solution of $Rf^1CO_2M^a$ is performed at the end of the salification step a), so as to remove the water formed during the reaction. Furthermore, the distillation step may also be followed by a drying step, especially in an oven at a temperature of between 30° C. and 100° C., preferentially under vacuum.

Preferably, the solution of $Rf^1CO_2M^a$ obtained after concentration comprises an amount of water of less than 10 000 ppm, preferably less than 1000 ppm and preferentially less than 500 ppm.

Sulfination Step b)

In the context of the invention, the process for preparing $(Rf^1SO_2)(Rf^2SO_2)NM^b$ and especially $(Rf^1SO_2)(Rf^2SO_2)_2NLi$ may comprise a step b) of sulfination of $Rf^1CO_2M^a$ to $Rf^1SO_2M^a$.

In the context of the invention, and unless otherwise mentioned, the term "sulfination" means the reaction directed toward preparing $Rf^1SO_2M^a$ from $Rf^1CO_2M^a$. Mention may be made, for example, of the sulfination reaction of potassium trifluoroacetate $(CF_3CO_2K)$ to potassium triflinate $(CF_3SO_2K)$ or the sulfination reaction of $C_2F_5SO_2K$ from $C_2F_5CO_2K$.

According to one embodiment, $M^a$ represents K. Thus, preferably, $Rf^1SO_2M^a$ is $Rf^1SO_2K$.

The step of sulfination of $Rf^1CO_2M^a$ to $Rf^1SO_2M^a$ may be performed according to the processes known to those skilled in the art. The sulfination reaction b) according to the invention may especially be performed under the conditions described in FR 2 900 403, FR 2 732 010 or FR 2 732 016.

According to one embodiment, the sulfination step b) of the process consists in reacting $Rf^1CO_2M^a$ with a sulfur oxide.

According to the invention, the sulfur oxide, preferably sulfur dioxide, may be used in gaseous form. It may also be introduced in solution form, in the organic solvent chosen for the reaction (reaction solvent), at a concentration generally ranging between 1% and 10% by weight and preferably between 3% and 6%.

Preferably, the sulfination reaction is performed in the presence of $SO_2$ in gaseous form.

According to one embodiment, the ratio between the number of moles of sulfur oxide and the number of moles of $Rf^1CO_2M^a$, and especially of $CF_3CO_2K$ ranges from 0.1 to 5 and preferably from 1 to 3. Preferentially, the ratio is about 2.

The sulfination step b) of the process of the invention may be performed in an aprotic organic solvent. Preferably, the solvent used in the sulfination step is a polar aprotic solvent. Preferably, the polar aprotic solvent comprises very few impurities bearing acidic hydrogen.

In the context of the invention, and unless otherwise mentioned, the term "aprotic solvent" means a solvent which, in the Lewis theory, does not have any protons to release.

According to one embodiment, the solvent used makes it possible to dissolve the $Rf^1CO_2M^a$ at least partially and preferably completely. Preferably, the polar aprotic solvent that may be used has a significant dipolar moment. Thus, its relative dielectric constant $\in$ is advantageously at least equal to about 5. Preferably, its dielectric constant is less than or equal to 50 and greater than or equal to 5, and is especially between 30 and 40.

In order to determine whether the organic solvent satisfies the dielectric constant conditions stated above, it is possible to refer, inter alia, to the tables of the publication: Techniques of Chemistry, II—Organic solvents—p. 536 et seq., $3^{rd}$ edition (1970).

According to one embodiment, the organic solvent for the sulfination step is capable of solvating the cations, which means that the solvent has certain basicity properties within the Lewis meaning. In order to determine whether the solvent satisfies this requirement, its basicity is assessed by referring to the "donor number". In particular, the polar organic solvent used has a donor number of greater than 10 and preferably greater than or equal to 20. Preferably, the organic solvent has a donor number of between 10 and 30.

In the context of the invention, and unless otherwise mentioned, the term "donor number" denotes, in abbreviated form DN, a number which gives an indication regarding the nucleophilic nature of the solvent and reveals its ability to give its lone pair.

In the publication by Christian REICHARDT, [Solvents and Solvent Effects in Organic Chemistry—VCH p. 19 (1990)], the definition of the "donor number" is given as being the negative ($-\Delta H$) of the enthalpy (Kcal/mol) of interaction between the solvent and antimony pentachloride in a dilute solution of dichloroethane.

In the sulfination step b) of the present invention, the polar solvent(s) may be free of acidic hydrogen; in particular when the polar nature of the solvent(s) is obtained by the presence of electron-withdrawing groups, it is desirable for there not to be any hydrogen on the atom in the position $\alpha$ of the electron-withdrawing function.

More generally, it is preferable for the pKa corresponding to the first acidity of the solvent to be at least equal to about 20 ("about" stressing the fact that only the first figure of the tens values is significant), advantageously between 20 and 35 and preferably between 25 and 35.

The acidic nature may also be expressed by the acceptor number AN of the solvent, as defined by Christian REICHARDT, ["Solvents and Solvent Effects in Organic Chemistry", $2^{nd}$ edition, VCH (RFA), 1990, pages 23-24].

Advantageously, this acceptor number AN is less than 20 and in particular less than 18.

Solvents that satisfy the various requirements and that give good results in the sulfination step b) may especially be solvents of amide type. Among the amides, amides of particular nature such as tetrasubstituted ureas and monosubstituted lactams are also included. The amides are preferably substituted (disubstituted for the ordinary amides). Mention may be made, for example, of pyrrolidone derivatives, such as N-methylpyrrolidone (NMP), or N,N-dimethylformamide (DMF) or N,N-dimethylacetamide.

Another particularly advantageous category of solvents consists of ethers, whether they are symmetrical or asymmetrical, and whether they are open or closed. Various glycol ether derivatives such as the various glymes, for example diglyme, should be incorporated in the ether category.

Preferentially, DMF is the solvent used in the sulfination step b).

According to the invention, the implementation may be performed batchwise or continuously.

In a batchwise implementation embodiment, $Rf^1CO_2M^a$ is introduced into the organic solvent and the sulfur oxide is then added in total or in fractions.

According to the invention, the sulfination reaction may be performed in a standard reactor equipped with a heating device (heat exchanger) and a stirring device, for example stirring using an impeller. The reaction mixture is then heated.

In a continuous embodiment, use is made of apparatus allowing continuous implementation, such as several reactors in cascade or a tube equipped with a jacket in which circulates a heat-exchange fluid whose characteristics make it possible to reach the desired reaction temperature.

In this case, the device may be fed with $Rf^1CO_2M^a$ as a mixture with the organic solvent and sulfur dioxide may then be introduced. The latter may be added to the feed solution comprising the $Rf^1CO_2M^a$ and the organic solvent, or it may be introduced into different points of the apparatus: the introduction may be made into the top of the reactor or into the reaction mass.

Next, heating may be performed until the desired degree of conversion is obtained.

According to one embodiment, the sulfination step b) may be performed at a temperature ranging from 100° C. to 200° C., preferably from 110° C. to 180° C. and preferentially from 120° C. to 150° C. Preferably, the sulfination reaction is performed at 140° C.

The sulfination reaction is advantageously performed at atmospheric pressure, but higher pressures may also be used. Thus, the reaction may be performed at an absolute total pressure chosen between 1 and 20 bar (100 to 2000 kPa) and preferably between 1 and 3 bar (100 to 300 kPa).

The heating time may vary widely as a function of the chosen reaction temperature. In particular, the reaction is performed for about 30 minutes to 24 hours, preferably for two hours to less than 20 hours and more preferentially for 4 hours to 5 hours.

When said sulfur oxide is sulfur dioxide, the resulting mixture from the sulfination step b) may comprise two phases: a liquid phase, in which at least part of said $Rf^1CO_2M^a$ and of the sulfur dioxide are dissolved in said solvent, and a gaseous phase essentially containing sulfur dioxide and carbon dioxide formed during the reaction.

To avoid excessive degradation of the final product, and thus to ensure good reaction selectivity, it is preferable not to seek to fully convert the starting $Rf^1CO_2M^a$. The reaction progress may be monitored by the degree of conversion (DC) of the $Rf^1CO_2M^a$, which is the mole ratio of the amount of $Rf^1CO_2M^a$ disappeared to the initial amount of $Rf^1CO_2M^a$ in the reaction medium, this degree being readily calculated after assay of the acid remaining in the medium.

Preferably, the sulfination reaction is performed until a degree of conversion of greater than 30% is obtained, expressed by the mole ratio of the desired product $Rf^1SO_2M^a$/$Rf^1CO_2M^a$ converted.

In the context of the invention, and unless otherwise mentioned, the term "degree of conversion (DC)" means the ratio between the number of moles of substrate converted and the number of moles of substrate engaged.

In the context of the invention, and unless otherwise mentioned, the term "yield (RY)" means the ratio between the number of moles of product formed and the number of moles of substrate engaged.

In the context of the invention, and unless otherwise mentioned, the term "selectivity (RC)" means the ratio between the number of moles of product formed and the number of moles of substrate converted during the reaction.

In the context of the invention, the process may comprise a depressurization step after the sulfination step b).

According to one embodiment, the sulfination step b) leads to a mixture M consisting especially of a solution of unconverted $Rf^1CO_2M^a$ and of $Rf^1SO_2M^a$ formed, in the reaction solvent, especially in DMF.

According to one embodiment, the mixture M obtained after step b) is subjected to a step of distillation of the reaction solvent, especially of the DMF. Advantageously, the reaction solvent distilled off may be recycled and reused in the sulfination step b).

Step of Separation of the Salts and Recycling of the Organic Solvent b1)

In the context of the invention, the process according to the invention may comprise, after the sulfination step b), a step 1) of separation of the salts and recycling of the organic solvent, for example by liquid/liquid extraction.

The extraction step b1) may be performed according to the processes known to those skilled in the art.

According to one embodiment, step b1) is performed by adding water and an extraction solvent to the reaction medium resulting from the preceding step.

Preferably, the extraction solvent is a chlorinated solvent, chosen especially from dichloromethane, chloroform, carbon tetrachloride, 1,2-dichloroethane, trichloroethylene and perchloroethylene, and also chlorinated aromatic solvents (chlorobenzene, 1,2-dichlorobenzene and higher homologs). Preferably, the extraction solvent is dichloromethane.

In the context of the invention, a two-phase medium may be obtained containing an organic phase O3 and a saline aqueous phase A3, after separation of said phases by settling.

According to one embodiment, phase O3 comprises the extraction solvent, especially dichloromethane, and also the organic solvent used in the sulfination step b), especially DMF.

In the context of the invention, phases O3 and A3 may be separated after settling of the phases, by step b1) of liquid/liquid extraction of said phases.

Preferably, phase O3 has a density less than that of the aqueous phase A3.

In the context of the invention, phase O3 may be subjected to a distillation step for separately recovering the extraction solvent, especially dichloromethane, and the organic solvent used in the sulfination step b), especially DMF. The various solvents may be collected separately as a result of their different boiling points.

According to one embodiment, the aqueous phase A3 comprises a mixture M3 comprising $Rf^1CO_2M^a$ and $Rf^1SO_2M^a$.

The process according to the invention may comprise a step of recycling the solvent used in the sulfination step b), especially DMF, obtained by distillation of phase O3. The solvent thus recycled may be reinjected into the process, especially into the sulfination step b).

The process according to the invention may also comprise a step of recycling the extraction solvent, especially dichloromethane, obtained by distillation of phase O3. The extraction solvent thus recycled may be reinjected into the process, namely into step b1).

In the context of the invention, and unless otherwise mentioned, the term "recycled solvent" means a solvent which has undergone a recycling step.

This step b1) may advantageously allow recovery of the salts $Rf^1CO_2M^a$ (not converted in the sulfination step) and $Rf^1SO_2M^a$ (formed), in an aqueous phase, especially in the aqueous phase A3.

Furthermore, the use of an extraction solvent advantageously makes it possible to remove the organic solvent used in the sulfination step b).

The process for preparing $(Rf^1SO_2)(Rf^2SO_2)NM^b$ and especially $(CF_3SO_2)_2NLi$ according to the invention advantageously comprises steps of recycling of solvents, such as the extraction solvent of the extraction step b1) or the reaction solvent of the sulfination step b).

Oxidation Step c)

The process for preparing $(Rf^1SO_2)(Rf^2SO_2)NM^b$ according to the invention may comprise a step c) of oxidation of the aqueous phase A3 as defined above, to give $Rf^1SO_2X$, X representing a chlorine, fluorine or bromine atom.

According to one embodiment, $Rf^1SO_2X$ is $CF_3SO_2X$, X being as defined above.

In particular, the step of oxidation of the aqueous phase A3 corresponds to the oxidation of the mixture M3 comprising $Rf^1CO_2M^a$ and $Rf^1SO_2M^a$.

The oxidation step may be performed according to the processes known to those skilled in the art.

According to one embodiment, the step of oxidation of the aqueous phase A3 is performed in the presence of an oxidizing agent chosen from $SO_2F_2$, $F_2$, $Cl_2$, $SO_2Cl_2$, $Br_2$ and $SO_2Br_2$.

According to one embodiment, when the oxidizing agent is $SO_2Cl_2$ or $Cl_2$, the product formed is $Rf^1SO_2Cl$ and especially trifluoromethanesulfonyl chloride $CF_3SO_2Cl$.

According to another embodiment, when the oxidizing agent is $SO_2Br_2$ or $Br_2$, the product formed is $Rf^1SO_2Br$ and especially trifluoromethanesulfonyl bromide $CF_3SO_2Br$.

According to another embodiment, when the oxidizing agent is $SO_2F_2$ or $F_2$, the product formed is $Rf^1SO_2F$ and especially trifluoromethanesulfonyl fluoride $CF_3SO_2F$.

Preferably, the oxidizing agent is $Cl_2$ and the product formed in the oxidation step c) is $Rf^1SO_2Cl$.

According to the invention, the oxidation step may be performed at a temperature ranging from −40° C. to 20° C., preferably from −20° C. to 5° C. and preferentially from −5° C. to 0° C.

According to one embodiment, the step of oxidation of the aqueous phase A3 leads to a two-phase mixture M4 comprising an aqueous phase A4.

According to a particular embodiment, when the oxidizing agent is chosen from $SO_2F_2$ and $F_2$, the step of oxidation of the aqueous phase A3 leads to a mixture M4 comprising an aqueous phase A4 and a gaseous phase G4. In particular, the gaseous phase G4 comprises, and preferentially consists of, $Rf^1SO_2F$.

According to the invention, gaseous $Rf^1SO_2F$ may be condensed, especially at a temperature from about −80° C. to −30° C. Typically, condensed $Rf^1SO_2F$ may be purified by cryodistillation or treated with sulfuric acid.

According to another particular embodiment, when the oxidizing agent is chosen from $Cl_2$, $SO_2Cl_2$, $Br_2$ and $SO_2Br_2$, the step of oxidation of the aqueous phase A3 leads to a mixture M4 comprising, after separation of the phases by settling, an organic phase O4 and an aqueous phase A4. In particular, the organic phase has a density less than that of the aqueous phase A4.

Preferably, the organic phase O4 comprises $Rf^1SO_2X$, especially $Rf^1SO_2Cl$ or $Rf^1SO_2Br$, formed after the oxidation step c), which separates out by settling in the form of a water-immiscible liquid. Phase O4 may be subjected to a distillation step, so as to recover $Rf^1SO_2X$ and especially $Rf^1SO_2Cl$.

Preferably, said aqueous phase A4 comprises $Rf^1CO_2M^a$ and salts, especially halide salts. In particular, the halide salts are chosen from potassium chloride, potassium fluoride and potassium bromide. The nature of these halide salts depends especially on the nature of the oxidizing agent used. The $Rf^1CO_2M^a$ of phase A4 corresponds to the $Rf^1CO_2M^a$ of the aqueous phase A3, and more particularly of the mixture M3, which was not converted during the oxidation step c).

According to the process of the invention, phase A4 may contain from 1% to 45% by weight of $Rf^1CO_2M^a$, preferably from 5% to 30% and preferentially from 10% to 25%.

Typically, the organic phase O4 may be separated from the phase A4 by settling of the phases.

According to the invention, the compound $Rf^1SO_2F$ may be obtained by oxidation of a mixture M3, comprising $Rf^1CO_2M^a$ and $Rf^1SO_2M^a$, as defined above, or by electrofluorination of $R^hSO_2F$, $R^h$ representing a hydrocarbon-based chain identical to that of $Rf^1$, said chain comprising hydrogen atoms in place of the fluorine atoms. $R^hSO_2F$ being optionally obtained from $R^hSO_2W$, with W representing a halogen atom other than fluorine, namely Br, Cl or I, and preferably chlorine.

According to the invention, the compound $Rf^1SO_2F$ may also be obtained from $Rf^1SO_2Cl$. $Rf^1SO_2Cl$ may especially be obtained according to the processes described in WO 2008/111 418, WO 2009/060 815 and Jpn. Kokai Tokkyo Koho, 2010173959, Dec. 8, 2010.

Typically, the step of electrofluorination of $R^hSO_2F$ may be performed under the conditions known to those skilled in the art, and especially under the conditions described in U.S. Pat. No. 4,927,962.

Typically, the compound $R^hSO_2F$ may be prepared under the conditions known to those skilled in the art, and especially by halogen exchange using $R^hSO_2W$. W representing a halogen atom other than fluorine, preferably chlorine, the exchange conditions especially being described in U.S. Pat. No. 5,540,818.

In particular, $R^hSO_2F$ is $CH_3SO_2F$.

In particular, $R^hSO_2W$ is $CH_3SO_2Cl$.

According to one embodiment, $CF_3SO_2F$ is obtained by electrofluorination of $CH_3SO_2F$, $CH_3SO_2F$ being obtained by a halogen exchange reaction of $CH_3SO_2Cl$ in fluorinated aqueous medium, as described in U.S. Pat. No. 5,540,818.

According to the invention, the process according to the invention may comprise the recycling of $Rf^1CO_2M^a$. Specifically, $Rf^1CO_2M^a$ which was not converted during step c) of oxidation of the aqueous phase A3 may be recycled and reused in the process.

It was advantageously shown that the use of an oxidizing agent such as $Cl_2$ or $F_2$ makes it possible to act selectively on the compound $Rf^1SO_2M^a$ of a mixture containing $Rf^1SO_2M^a$ and $Rf^1CO_2M^a$, without acting on $Rf^1SO_2M^a$. Thus, $R^1CO_2M^a$ may advantageously be recycled. This makes it possible to upgrade $Rf^1CO_2M^a$ in the process and affords an overall saving for the process.

Step of Recycling of $Rf^1CO_2M^a$

Typically, the step of recycling of $Rf^1CO_2M^a$ may be performed under the conditions known to those skilled in the art, and especially under the conditions described in FR 2 924 116.

According to one embodiment, recycling of $Rf^1CO_2M^a$ comprises various steps, and especially a step of acidification of the aqueous solution A4 in an ether, to obtain a two-phase mixture M5.

According to the invention, the ether may be chosen from: anisole, diisopropyl ether (DIPE), methyl tert-butyl ether (MTBE), diphenyl ether and alkyl ethers such as n-butyl ether. Preferably, the ether is MTBE.

According to the invention, the acidification step may be performed with an acid chosen from hydrochloric acid, sulfuric acid, nitric acid and phosphoric acid. Preferably, the acid is hydrochloric acid.

According to one embodiment, the acid is added so as to acidify the aqueous solution A4 containing $Rf^1CO_2M^a$ down to a pH from 0 to 5, from 1 to 3 and preferentially down to a pH equal to 1.

According to one embodiment, the ether is added to the acidified aqueous solution.

According to the process of the invention, the two-phase mixture M5 obtained after the acidification step may comprise an organic phase O5 comprising the ether, and an aqueous phase A5 comprising salts, especially halide salts.

Preferably, the organic phase O5 also comprises $Rf^1CO_2H$ formed during the acidification step. In particular, phase O5 comprises a complex formed between the ether and $Rf^1CO_2H$.

According to one embodiment, phase O5 comprises from 10% to 70% by weight of $Rf^1CO_2H$ and preferably from 30% to 60% by weight.

Preferably, phase A5 comprises salts, especially halide salts, such as KF, KBr or KCl. The nature of these salts depends especially on the oxidizing agent used in the abovementioned oxidation step.

According to the invention, phases O5 and A5 may be separated by settling of the phases. Preferably, phase O5 has a density less than that of phase A5.

It has been shown that a complex forms between the ether and the $Rf^1CO_2H$ formed, which separates by settling and makes it possible to shift the equilibrium toward the formation of $Rf^1CO_2H$.

This acidification step advantageously makes it possible to purify $Rf^1CO_2H$, by separating it from the halide salts remaining in the aqueous phase A5.

The step of recycling of $Rf^1CO_2M^a$ may also comprise a step of converting the $Rf^1CO_2H$, formed during the acidification step, into $Rf^1CO_2M^a$. Typically, this step of converting $Rf^1CO_2H$ into $Rf^1CO_2M^a$ is a basification step.

According to one embodiment, an aqueous solution of an alkali metal hydroxide, especially KOH, is added to the preceding organic phase O5.

According to the invention, an aqueous solution of an alkali metal hydroxide, especially aqueous KOH, may be added to phase O5 until a final pH of greater than 7.5 is obtained.

After the step of basifying phase O5, a two-phase mixture M6 may be obtained.

Preferably, the mixture M6 comprises an organic phase O6 and an aqueous phase A6, the organic phase O6 comprising the ether used in the preceding acidification step, and phase A6 comprising $Rf^1CO_2M^a$ formed and the excess alkali metal hydroxide, especially KOH. Typically, these two phases are separated by settling.

According to the invention, phase O6 may be recycled. Preferably, phase O6, comprising the ether, is recycled to be reused in the acidification step as defined above.

In particular, phase A6 comprises from 5% to 55% by weight of $Rf^1CO_2M^a$, preferably from 5% to 45% by weight and preferentially from 10% to 40% by weight.

In the context of the invention, the step of recycling of $Rf^1CO_2M^a$ may comprise an additional step of neutralization of phase A6. In particular, this neutralization step consists in adding $Rf^1CO_2H$ to phase A6, to give an aqueous phase A7 of neutral pH.

According to one embodiment, the amount of $Rf^1CO_2H$ added to phase A6 is equal to the amount of alkali metal hydroxide, especially KOH, present in said phase A6.

In the context of the invention, and unless otherwise mentioned, phase A7 corresponds to phase A6 which has undergone a neutralization step. Phase A7 may be obtained by adding $Rf^1CO_2H$ to phase A6.

According to one embodiment, phase A7 comprises $Rf^1CO_2M^a$. In particular, phase A7 comprises from 5% to 50% by weight of $Rf^1CO_2M^a$, preferably from 8% to 45% by weight and preferentially from 10% to 40% by weight.

In the context of the invention, the step of recycling of $Rf^1CO_2M^a$ may comprise a step directed toward separating $Rf^1CO_2M^a$ from the aqueous phase A7.

Thus, the process may comprise a step of evaporating the water from phase A7.

Preferably, a precipitate of $Rf^1CO_2M^a$ is obtained, said precipitate comprising up to 10% by weight and preferably up to 7% by weight of water.

According to one embodiment, the step of recycling of $Rf^1CO_2M^a$ may comprise a step of adding an organic solvent, preferably an organic solvent as defined previously for the sulfination step, such as DMF or NMP. In particular, the organic solvent is DMF. Typically, the addition of DMF facilitates the evaporation of water remaining in the precipitate.

In particular, the addition of DMF to the precipitate of $Rf^1CO_2M^a$ may lead to a mixture M8 especially comprising water.

According to one embodiment, a step of evaporating the water from the mixture M8 is performed.

In the context of the invention, a solution O8 may be obtained after the step of evaporating the water from the mixture M8.

Preferably, the solution O8 is a solution of $Rf^1CO_2M^a$ in the organic solvent, especially in DMF. In particular, the solution O8 comprises from 10% to 60% by weight of $Rf^1CO_2M^a$ and preferably from 20% to 50% by weight.

According to the invention, the solution O8 may comprise an amount of water of less than 500 ppm and preferentially less than 300 ppm. In particular, the solution O8 comprises an amount of water of less than 200 ppm.

In the context of the invention, the solution O8 of $Rf^1CO_2M^a$ in the organic solvent, especially DMF, may be recycled into the process for preparing $(Rf^1SO_2)(Rf^2SO_2)NM^b$, and especially $(CF_3SO_2)_2NLi$. In particular, the solution O8 may be reused in the sulfination step b).

Ammonolysis Step d)

In the context of the invention, the process for preparing $(Rf^1SO_2)(Rf^2SO_2)NM^b$ may comprise a step d) of ammonolysis of $Rf^1SO_2X$ as defined previously.

The step of ammonolysis of $Rf^1SO_2X$ may be performed according to the processes known to those skilled in the art.

Preferably, $Rf^1SO_2X$ is such that X represents a halogen atom, especially Br, Cl or F. In particular, $Rf^1SO_2X$ is $Rf^1SO_2Cl$ or $Rf^1SO_2F$, and preferentially $Rf^1SO_2X$ is $Rf^1SO_2Cl$.

The ammonolysis reaction may especially be performed under the conditions described in FR 2 763 331 or FR 2 724 380.

According to one embodiment, the ammonolysis step is performed according to two different procedures, such as those described in FR 2 724 380, each of the two modes possibly leading to symmetrical or dissymmetrical sulfonimides.

According to the invention, the ammonolysis step may be performed:

iii) either in the presence of $Rf^1SO_2X$ and $Rf^2SO_2X$, of $NH_3$ and of a base chosen from tertiary amines, trialkylphosphines, hindered dialkylphosphines, phosphonium hydroxides, hindered dialkylamines, trialkylamines, ammonium hydroxides, and phosphorus-bearing and nitrogen-bearing rings of suitable basicity;

iv) or in the presence of $Rf^1SO_2X$, of a sulfonamide of formula $Rf^2SO_2NH_2$, $Rf^1$ and $Rf^2$ which may be identical or different, and of a base as defined above according to method iii).

According to the invention, the ammonolysis step may lead to a triflimide having the following formula: $[(Rf^1SO_2)_2N^-, R'_3NH^+]$ or $[(Rf^1SO_2)(Rf^2SO_2)N^-, R'_3NH^+]$, in which $Rf_1$ and $Rf_2$ may be identical or different.

Respecting the stoichiometry of the ammonolysis reaction is desirable as regards $Rf^1SO_2X$ and the base used. Nevertheless, the ammonolysis reaction may be performed successfully using an excess of base.

According to the invention, the ammonolysis reaction according to method iii) may be performed in the presence of at least three equivalents of base, and:

either at least two equivalents of $Rf^1SO_2X$, especially $Rf^1SO_2Cl$, or at least one equivalent of $Rf^1SO_2X$ and at least one equivalent of $Rf^2SO_2X$, $Rf^1$ and $Rf^2$ being identical or different.

According to the invention, $Rf^2SO_2X$ may be obtained under the same conditions as those used for preparing $Rf^1SO_2X$ as described above.

According to the invention, $Rf^2SO_2NH_2$ may be obtained according to the processes known to those skilled in the art, and especially under the conditions described by Foropoulos et al. (*Inorganic Chemistry*, 1984, vol. 23, No. 23, pp. 3720-3723). In particular, $Rf^2SO_2NH_2$ is advantageously prepared by reacting $Rf^2SO_2X$ (X=halogen, especially F, Cl and Br) with ammonia at −78° C.

Thus, the use of at least two equivalents of $Rf^1SO_2X$ may lead to a symmetrical sulfonimide salt $(Rf^1SO_2)_2NM^b$. Depending on the stoichiometry of the reaction, mechanically the use of at least one equivalent of $Rf^1SO_2X$ and of at least one equivalent of $Rf^2SO_2X$ may lead to a symmetrical sulfonimide salt $(Rf^1SO_2)(Rf^2SO_2)NM^b$ in which $Rf^1$ and $Rf^2$ are identical, or to a dissymmetrical sulfonimide salt: $(Rf^1SO_2)(Rf^2SO_2)NM^b$ in which $Rf^1$ and $Rf^2$ are different.

According to the invention, depending on its stoichiometry, the ammonolysis reaction of method iv) may be performed in the presence of at least one equivalent of $Rf^1SO_2X$, especially $Rf^1SO_2Cl$, of at least one equivalent of $Rf^2SO_2NH_2$ and of at least two equivalents of base.

Thus, the ammonolysis method iv) may lead to a symmetrical sulfonimide salt $(Rf^1SO_2)(Rf^2SO_2)NM^b$ (or $(Rf^1SO_2)_2NM^b$) in which $Rf^1$ and $Rf^2$ are identical, or to a dissymmetrical sulfonimide salt $(Rf^1SO_2)(Rf^2SO_2)NM^b$ in which $Rf^1$ and $Rf^2$ are different.

According to the invention, the ammonolysis step performed under the conditions of method iii) may lead to a symmetrical triflimide having the following formula $[(Rf^1SO_2)_2N^-, R'_3NH^+]$ or to a dissymmetrical triflimide having the following formula $[(Rf^1SO_2)(Rf^2SO_2)N^-, R'_3NH^+]$.

According to the invention, the ammonolysis step performed under the conditions of method iv) may lead to a triflimide having the formula $[(Rf^1SO_2)(Rf^2SO_2)N^-, R'_3NH^+]$, said triflimide being symmetrical (when $Rf^1$ and $Rf^2$ are identical) or dissymmetrical (when $Rf^1$ and $Rf^2$ are different).

Thus, in general, the ammonolysis step according to the invention, irrespective of the method used, may lead to a triflimide of formula $[(Rf^1SO_2)(Rf^2SO_2)N^-, R'_3NH^+]$ in which $Rf^1$ and $Rf^2$ are identical or different.

According to the invention, the ammonolysis reaction may be performed in an organic solvent or in the absence of organic solvent, independently of the method used (method iii) or iv)).

According to one embodiment, the organic solvent is advantageously sparingly polar, of the type such as chlorinated solvents, nitriles, ethers or aromatic solvents. Preferably, the solvent is dichloromethane.

According to the invention, the ammonolysis reaction may be performed in the presence or absence of a catalyst.

According to one embodiment, when the ammonolysis step is performed under the conditions of method iii), a catalyst, such as dimethylaminopyridine (DMAP), is used.

According to one embodiment, when the ammonolysis step is performed under the conditions of method iv), no catalyst is used.

According to the invention, the ammonolysis reaction may be performed at atmospheric pressure or under pressure, and especially in at least liquid and/or gaseous phase.

According to one embodiment, the ammonolysis reaction is performed in a tubular reactor under pressure.

According to the invention, $NH_3$, preferentially used for performing one of the methods iii or iv), may be in gas form or in the form of an aqueous or anhydrous solution.

According to one embodiment, the base is a tertiary amine of formula $NR'_3$, in which R' represents a linear or branched alkyl group containing from 1 to 20 carbon atoms. Preferably, the tertiary amine is chosen from triethylamine (TEA), triisopropylamine, dicyclohexylethylamine and diisopropylethylamine (DIPEA). Preferably, the base used is diisopropylethylamine or triethylamine.

Use is made in particular of diisopropylethylamine when $Rf^1SO_2X$ is $Rf^1SO_2Cl$ or $Rf^1SO_2Br$, preferably $Rf^1SO_2Cl$, and triethylamine when $Rf^1SO_2X$ is $Rf^1SO_2F$.

According to one embodiment, when the ammonolysis reaction is performed with diisopropylethylamine, the ammonolysis step leads to the complex $[(Rf^1SO_2)_2N^-, NEt(i-Pr)_2H^+]$ or to the complex $[(Rf^1SO_2)(Rf^2SO_2)N^-, NEt(i-Pr)_2H^+]$.

According to another embodiment, when the ammonolysis reaction is performed with triethylamine, the ammonolysis step leads to the following complex: $[(Rf^1SO_2)_2N^-, NEt_3H^+]$ or $[(Rf^1SO_2)(Rf^2SO_2)N^-, NEt_3H^+]$ According to one embodiment, the ammonolysis reaction is performed as follows: a solution of $Rf^1SO_2Cl$ and of $Rf^2SO_2Cl$ in dichloromethane is added to a medium containing diisopropylethylamine, a catalyst, dichloromethane and ammonia. In particular, the solution of $Rf^1SO_2Cl$ and of $Rf^2SO_2Cl$ is added at a temperature ranging from −20° C. to 10° C. The reaction medium is then stirred at room temperature for a minimum of one hour.

According to the invention, $Rf^2SO_2Cl$ may be prepared under the same conditions as for $Rf^1SO_2Cl$ as described above, or according to the processes known to those skilled in the art.

According to another embodiment, the ammonolysis reaction is performed as follows: $Rf^1SO_2F$ and $Rf^2SO_2F$ are introduced with ammonia into a medium containing triethylamine, at a temperature ranging from −80° C. to −30° C., preferably from −60° C. to −40° C. and preferentially at about −50° C. The reaction medium is then stirred at a temperature ranging from 20° C. to 80° C. and preferably from 50° C. to 70° C., for the time necessary for the reaction to be complete. In particular, the reaction medium is stirred at 65° C. for 24 hours.

According to one embodiment, the ammonolysis step comprises at least one step of washing with water. If the reaction was performed with $Rf^1SO_2F$, and $Rf^2SO_2F$, an organic solvent, such as dichloromethane, is added to the medium for the step of washing with water.

According to the invention, $Rf^2SO_2F$ may be prepared under the same conditions as for $Rf^1SO_2F$ as described above, or according to the processes known to those skilled in the art.

Thus, the ammonolysis step may lead to a two-phase mixture M9, comprising an organic phase O9 and an aqueous phase A9.

In particular, the organic phase O9 comprises the complex $[(Rf^1SO_2)(Rf^2SO_2)NH,R'_3N]$, such as $[(Rf^1SO_2)(Rf^2SO_2)NH,NEt(i-Pr)$ or $[(Rf^1SO_2)(Rf^2SO_2)NH,NEt_3$ dichloromethane, and also organic impurities formed during the various steps of the process, such as the sulfination step b), the oxidation step c) and/or the ammonolysis step d). In particular, the organic impurities present in the organic phase O9 are the salts $Rf^1SO_2NH_2,R'_3N$ and/or $(Rf^2SO_2)NH_2,R'_3N$, $Rf^1SO_2H,R'_3N$ and/or $Rf^2SO_2H,R'_3N$ and $Rf^1SO_3H,R'_3N$ and/or $Rf^2SO_3H,R'_3N$. In particular, when triethylamine is used, the organic impurities are $Rf^1SO_2NH_2,NEt_3$, $(Rf^2SO_2)NH_2,NEt_3$, $Rf^1SO_2H,NEt_3$, $Rf^2SO_2H,NEt_3$, and $Rf^1SO_3H,NEt_3$ and $Rf^1SO_3H,NEt_3$. In particular, when diisopropylamine is used, the organic impurities are $Rf^1SO_2NH_2,NEt(i-Pr)_2$, $(Rf^2SO_2)NH_2,NEt(i-Pr)_2$, $Rf^1SO_2H,NEt(i-Pr)_2$, $Rf^2SO_2H,NEt(i-Pr)_2$, and $Rf^1SO_3H,NEt(i-Pr)_2$ and $Rf^1SO_3H,NEt(i-Pr)_2$.

The washing step advantageously makes it possible to reduce the amount of chlorides, bromides or fluorides present in the organic phase O9.

According to one embodiment, phase A9 comprises the ammonium sulfonylimides, especially the ammonium perfluoroalkylsulfonylimides, formed during the ammonolysis step and the ammonium salts of fluorine, bromine or chlorine.

In particular, phase A9 comprises diisopropylamine hydrochloride when diisopropylamine has been used in the ammonolysis step or triethylamine hydrofluoride when triethylamine has been used.

The process according to the invention may comprise a step of treating the aqueous phase A9. In particular, the treatment step is performed in the presence of 30% sodium hydroxide. In particular, this step makes it possible to recover the base $R'_3N$, and especially the diisopropylamine or the triethylamine, by neutralization with sodium hydroxide of the diisopropylethylamine hydrochloride or of the triethylamine hydrofluoride contained in the aqueous phase A9. The base, especially diisopropylamine or triethylamine, may thus be advantageously recovered and recycled in the process of the invention, and especially into the ammonolysis step.

According to one embodiment, the ammonolysis step may comprise a step of distilation of the reaction solvent, especially the dichloromethane. In particular, said solvent may be recycled into the process, especially into the ammonolysis step d).

Acidification Step e)

In the context of the invention, the process for preparing $(Rf^1SO_2)(Rf^2SO_2)NM^b$ and especially $(CF_3SO_2)_2NLi$ may comprise a step e) of acidification, and especially of the organic phase O9.

The acidification step may be performed according to the processes known to those skilled in the art.

According to one embodiment, the acidification step e) is performed on the organic phase O9 which has undergone a preliminary step of distillation of the organic solvent.

According to one embodiment, the acidification step may be performed in the presence of an acid chosen from the group consisting of: hydrochloric acid, sulfuric acid, phosphoric acid and nitric acid. Preferably, the acidification step is performed with sulfuric acid, especially 92% sulfuric acid.

According to one embodiment, the acidification step makes it possible to neutralize the complex $(Rf^1SO_2)$$(Rf^2SO_2)NH,NR'_3$, such as $(Rf^1SO_2)(Rf^2SO_2)NH,EtN(i-Pr)_2$ or $(Rf^1SO_2)(Rf^2SO_2)NH,NEt_3$, formed after the preceding ammonolysis step, to give the mixture M'1 as defined above.

In particular, the mixture M'1 comprises $(Rf^1SO_2)$$(Rf^2SO_2)NH$, and side products (organic and mineral impurities) such as the hydrogen sulfate of the tertiary amine base, $Rf^1SO_2H$ and/or $Rf^2SO_2H$, $Rf^1SO_3H$ and/or $Rf^2SO_3H$, $Rf^1SO_2NH_2$ and/or $Rf^2SO_2NH_2$, HCl, HBr or HF.

Preferably, the hydrogen sulfate of the tertiary amine base is diisopropylethylamine hydrogen sulfate ($H_2SO_4,NEt$ $(i-Pr)_2$) or triethylamine hydrogen sulfate ($H_2SO_4,NEt_3$).

According to the process of the invention, the mixture M'1 may be subjected to a distillation step as defined previously. In particular, the step of distilling the mixture M'1 gives the mixture M1.

According to one embodiment, the mixture M'1 which has undergone a distillation step especially comprises diisopropylethylammonium or triethylammonium hydrogen sulfate. This product may be diluted in water and treated with aqueous sodium hydroxide to form, respectively, diisopropylamine or triethylamine. In particular, the diisopropylamine or the triethylamine recovered may be distilled in the form of its azeotrope with water, to form a two-phase mixture comprising an aqueous phase and an organic phase. In particular, the organic phase comprises virtually pure diisopropylamine or triethylamine, which is recycled into the process, and especially into the ammonolysis step d).

Oxidation Step f)

The process according to the invention may also comprise a step of oxidizing the mixture M1 as defined previously. In particular, step f) of oxidizing the mixture M1 gives the mixture M2, these two mixtures being as defined above.

According to the invention, the oxidation step f) corresponds to step i) as described previously.

In accordance with the invention, the process of the invention comprises a step ii) of distilling the mixture M2, said distillation step being as defined previously, to give aqueous $(Rf^1SO_2)(Rf^2SO_2)NH$.

Neutralization Step g)

The process according to the invention may also comprise, after the distillation step ii), a step of neutralization of the aqueous $(Rf^1SO_2)(Rf^2SO_2)NH$.

The neutralization step may be performed under the conditions known to those skilled in the art.

According to one embodiment, the neutralization step is performed in the presence of an alkaline base, to give an aqueous solution of $(Rf^1SO_2)(Rf^2SO_2)Nm^b$.

According to one embodiment, the alkaline base is a lithium, potassium, sodium or cesium base.

In particular, the alkaline base is a lithiated base, chosen from the group consisting of: LiOH, LiH, LiOH.H$_2$O and Li$_2$CO$_3$. Preferably, the base used is LiOH.H$_2$O.

According to one embodiment, the step of neutralization of aqueous $(Rf^1SO_2)(Rf^2SO_2)NH$ is performed at a temperature below 35° C.

According to one embodiment, $(Rf^1SO_2)(Rf^2SO_2)NM^b$ and especially $(CF_3SO_2)_2NLi$ is obtained in the form of an aqueous solution.

Drying Step h)

The process according to the invention may also comprise a step h) of drying of the aqueous solution of $(Rf^1SO_2)(Rf^2SO_2)NM^b$ and especially $(CF_3SO_2)_2Li$ as defined above.

The drying step may be performed under the conditions known to those skilled in the art.

According to one embodiment, the process for preparing $(Rf^1SO_2)(Rf^2SO_2)NM^b$ comprises a step of drying the aqueous solution $(Rf^1SO_2)(Rf^2SO_2)NM^b$. Thus, $(Rf^1SO_2)(Rf^2SO_2)NM^b$ is preferentially dried by spraying. More rigorous drying may be obtained by evaporation using a rotary evaporator, under vacuum, and then in an oven at 100° C. under vacuum (5-25 mbar). The drying step makes it possible to obtain $(Rf^1SO_2)(Rf^2SO_2)NM^b$ in solid form.

According to one embodiment, $(Rf^1SO_2)(Rf^2SO_2)NM^b$ is obtained after the drying step, in a purity of greater than 99% and preferably greater than 99.5%.

It has been advantageously shown that the process of the invention makes it possible to prepare a solution of $(Rf^1SO_2)(Rf^2SO_2)NH$ in high purity, especially greater than 99.5%. Thus, the aqueous solution of $(Rf^1SO_2)(Rf^2SO_2)NH$ advantageously allows the preparation of $(Rf^1SO_2)(Rf^2SO_2)NM^b$, and especially $(Rf^1SO_2)(Rf^2SO_2)NLi$, in high purity, especially greater than 99.5%.

The process according to the invention advantageously allows the preparation of an aqueous solution of $(Rf^1SO_2)(Rf^2SO_2)NH$ free of organic impurities such as $Rf^1SO_2NH_2$ and/or $Rf^2SO_2NH_2$. Furthermore, the process according to the invention advantageously makes it possible to recycle $Rf^1SO_2NH_2$ and/or $Rf^2SO_2NH_2$ into the process.

The process according to the invention advantageously allows the preparation of pure $(Rf^1SO_2)(Rf^2SO_2)NM^b$ not having any coloration.

The process according to the invention can advantageously avoid the use of toxic and flammable solvents.

The examples that follow may illustrate the invention without, however, limiting it.

EXAMPLES

Abbreviations

[$(CF_3SO_2)_2NH$]: bis(trifluoromethane)sulfonimide (TFSIH)
[$(CF_3SO_2)_2NLi$]: lithium bis(trifluoromethane)sulfonimide (LiTFSI)
$CF_3SO_2NH_2$: trifluorosulfonamide (TFSAH)
$CF_3SO_2F$: trifluoromethanesulfonyl fluoride (TFSF)
$CF_3SO_2Cl$: trifluoromethanesulfonyl chloride (TFSCl)
$CF_3SO_2Br$: trifluoromethanesulfonyl bromide (TFSBr)
$CF_3CO_2K$: potassium trifluoroacetate (TFAK)
$CF_3SO_2K$: potassium triflinate (TFSK)
$CF_3CO_2H$: trifluoroacetic acid (TFA)
$CF_3SO_2H$: triflinic acid (TFSH)
$CF_3SO_3H$: trifluoromethanesulfonic acid (triflic acid, TA)
$CH_3SO_2Cl$: mesyl chloride (MsCl)
$CH_3SO_2F$: mesyl fluoride (MsF)
DIPEA: diisopropylethylamine
TEA: triethylamine Example 1

Step a:

TFAK (1.04 kg) was prepared by neutralizing aqueous potassium hydroxide solution (while maintaining a temperature of less than 25° C.), followed by evaporation of the corresponding solution and drying of the crystals obtained. TFAK was obtained in a purity of greater than 99%.

Step b:

A solution of TFAK (0.913 kg, i.e. 6 mol) in DMF (5.22 kg) was placed in a prewashed and dried 15 L autoclave. SO$_2$ was then added to the TFAK/DMF solution by sparging, and the exact amount introduced (0.768 kg, i.e. molar SO$_2$/TFAK ~2 l) was determined by weighing. The reactor was then closed and heated with stirring at 140° C. for 4 to 5 hours. After returning to room temperature, the reactor was degassed, and its contents were transferred into a 10 L glass vessel. After suitable dilution, ion chromatographic analysis of the reaction mass gave the following results:

Weight balance: 97% (weight collected: 6.7 kg)
Conversion of the TFAK (molar): 64%±2.5% (TFAK assayed in the reaction medium: 0.326 kg)
Yield of TFSK (molar): 50%±2.5% (TFSK assayed in the reaction medium: 0.517 kg)

The preceding crude reaction product (mixture of TFAK and TFSK) (6.5 kg) was then concentrated under vacuum to give 4.1 kg of DMF, recycled into the following operation, and with a residue (2.02 kg) discharged into the following step.

Step c:

Water (2 kg) was added to the concentrated crude reaction product from the preceding step (b) (about 2 kg) and the resulting solution was then extracted with dichloromethane to give:

an aqueous phase (2.4 kg) containing 0.236 kg of TFAK and 0.471 kg of TFSK and less than 1000 ppm of DMF; and an organic phase composed essentially of dichloromethane and DMF, distillation of which makes it possible successively to recover the dichloromethane and then the DMF, which are recycled into the process.

The preceding aqueous phase was placed in a 3 L glass reactor, cooled to 0° C., and gaseous dichlorine was then introduced. The TFSCl was recovered after separation of the reaction medium by settling, and then purified by distillation at atmospheric pressure to give pure TFSCl (0.422 kg, RY of 91 mol %).

The aqueous phase obtained, containing essentially TFAK and KCl, was extracted with a DIPE (diisopropyl ether)/HCl mixture to give, after separation of the phases by settling, an organic phase consisting of TFA, water and DIPE. The organic phase obtained was then back-extracted with aqueous potassium hydroxide to give an aqueous solution of TFAK, which was recycled into the process.

Step d:

The following were placed in a 5 L glass reactor: 323 g (2.5 mol) of DIPEA (diisopropylethylamine), 15.3 g (0.125 mol) of DMAP (4-dimethylaminopyridine) and 0.8 L of dichloromethane. The corresponding reaction medium was cooled to −15° C. and ammonia gas (25.5, 1.5 mol) was introduced. The exact amount introduced was determined by weighing. The solution of $CF_3SO_2Cl$ (674 g at 50 w/w % in $CH_2Cl_2$ (2 mol)) was then injected via a syringe plunger while keeping the temperature of the reaction mass at about 0° C. The temperature was then raised to 20° C. The reaction mass was then washed with water, to stabilize the reaction mass and to have two readily analyzable homogeneous phases. About 2.1 kg of organic phase and 0.540 kg of aqueous phase were recovered.

Step e:

The organic phase from the preceding step (d) was concentrated by distillation of the dichloromethane (1.4 kg), which was then recycled into the process. The distillation residue was then treated with concentrated sulfuric acid (0.920 kg). Distillation under reduced pressure made it possible to isolate the "crude" TFSIH (0.246 kg) (corresponding to the mixture M1 with triflinic acid (3.8 mol %) and triflic acid (3.5 mol %) and trifluorosulfonamide (0.7 mol %)) in a molar purity of 92% and a mass purity of about 96%.

Step f:

The triflinic acid TFSH contained in the "crude" TFSIH (1.9 w/w %) was oxidized to triflic acid (TA) with 30% aqueous hydrogen peroxide solution in the following manner: the "crude" TFSIH from the preceding step e) was brought to 80° C. and 30% aqueous hydrogen peroxide solution (3.15 g) was then added. The analyses showed that virtually all the TFSH was converted (content: 0.04 w/w %) into triflic acid (content: 3.4 w/w %), whereas the TFSIH (content: 96 w/w %) and the TFSAH (content: 0.4 w/w %) were unaffected.

Step g:

The reaction medium from the preceding step f) (0.246 kg) (mixture M2) was supplemented with demineralized water (0.2 kg) and then placed in the boiler of distillation apparatus on which was mounted a distillation column comprising 14 physical plates. The reaction medium was brought to 90° C. under 20 to 60 mbar to full reflux. The water was then removed with a reflux rate of 5 to 15 and a temperature at the top of the column of 20° C. to 45° C. When the temperature in the middle of the column reached a temperature of 20° C. to 55° C., the head fraction was removed into another vessel with a reflux rate of from 5 to 15 and a temperature at the top of the column from 40° C. to 100° C. When the amount of the head fractions reached about 90% of the water contained in the starting TFSIH, the withdrawal and reflux pipes were brought to about 60° C., and the head fraction was collected until the fluoride content in the distillate was less than 20 ppm. The pressure was then lowered to a pressure of from 5 to 15 mbar and the reaction medium was brought to full reflux. The core fraction was then collected with a reflux rate of from 5 to 15 and a temperature at the top of the column of from 50° C. to 80° C. Removal of the core fraction was stopped when the boiler temperature reached a temperature of from 110° C. to 130° C.

After analysis, the core fractions were combined and diluted with water to give an aqueous solution of "pure" TFSIH (~70 w/w %, 0.315 kg) containing less than 20 ppm of fluorides, chlorides and sulfates and less than 500 ppm of cumulative organic impurities, expressed relative to the anhydrous product (TA:<50 ppm, TFSH and TFSAH<100 ppm).

Step h:

The reaction medium from the preceding step g) was brought to 20° C. in a jacketed 1 L glass reactor. Lithium hydroxide (33 g), in the form of the solid monohydrate (LiOH, $H_2O$), was added until the solution was neutral. The temperature of the reaction medium was maintained below 35° C. and the pH of the final solution was adjusted to neutrality.

Step i:

The aqueous solution from the preceding step h) was concentrated on a rotary evaporator under vacuum and then dried in an oven under vacuum, to give a white powder of LiTFSI (0.225 kg). The analyses of the LiTFSI obtained showed that it contains less than 100 ppm of water, less than 20 ppm of fluorides and sulfates, less than 15 ppm of chlorides, less than 10 ppm of sodium, less than 5 ppm of calcium, potassium and silicon, less than 2 ppm of iron and less than 1 ppm of nickel, boron, aluminum and magnesium.

Step j:

The waters from the washing of the reaction medium of step d) (0540 kg) were treated to give DIPEA (0.310 kg), which was recycled into the process.

The complex TFSIH-DIPEA was extracted from the sulfuric residues of step e) (1.5 kg) with dichloromethane. The organic fraction was then recycled into the step of dichloromethane concentration of step e). The DIPEA was distilled off in the form of its azeotrope with water, which separates on settling into an organic layer (0.16 kg) and an aqueous layer (0.315 kg). The organic layer, consisting of virtually pure DIPEA, could be recycled into the process.

Example 2

Steps a' and b': identical to steps (a) and (b) of Example 1

Step c':

An aqueous phase (0.5 kg), obtained under the same conditions as those described for the preceding step c) before oxidation, was placed in a jacketed 1 L glass reactor. The reaction medium was cooled to −5° C., and dilute gaseous difluorine (5 v/v % in nitrogen) was then introduced by mass while at the same time maintaining a temperature below −5° C. The gaseous triflyl fluoride formed was condensed in a glass vessel cooled with an acetone/cardice mixture (~−50° C.). The TFSF recovered (0.0450 kg, molar RY 52%) was transferred into a 316 L stainless-steel autoclave with a working volume of 0.1 L.

The resulting aqueous phase, containing essentially TFAK and KF, was extracted with a DIPE (diisopropyl ether)/HCl mixture to give, after separation of the phases by settling, an organic phase consisting of TFA, water and DIPE. The organic phase obtained was then back-extracted with aqueous potassium hydroxide to give an aqueous solution of TFAK, which was recycled into the process.

Step d':

8 g (0.079 mol) of TEA (triethylamine) were placed in a 25 ml C276 Hastelloy® alloy autoclave. The autoclave was then cooled to about −50° C., and 2.5 g (16 mmol) of triflyl fluoride obtained previously (step c')) and 0.114 g (6.7 mmol) of ammonia were then introduced. The autoclave was then closed and maintained at 65° C. for 24 hours. After returning to 20° C., the reaction mass was diluted with dichloromethane and washed with water to give two readily analyzable homogeneous phases. The calculated molar yields are:

TFSI$^-$: 74%
TFS$^-$: 6%
TA$^-$: 10%
TFSA$^-$: 4%

Steps e' to i': The subsequent treatment of the organic phase under conditions similar to those described in steps (e) to (i) of Example 1 makes it possible to isolate the LiTFSI of high purity (1.5 g, molar yield: 78%).

Example 3

Steps a"

Water (650 ml) and potassium fluoride (175 g) were placed in a jacketed 1 L glass reactor. The reaction medium was brought to 10-20° C. and mesyl chloride (MsCl: 350 g) was added while keeping the reaction medium at a temperature below 30° C. The mesyl fluoride (MsF) was collected by separation by settling and purified by distillation. In total, 275 g of MsF were obtained (94%).

Step b'':

The following were placed in a 2 L electrochemical cell equipped with nickel electrodes with a total anode surface area of 1050 cm$^2$:

HF: 0.6 L $CH_3SO_2F$: 100 g (over 24 hours)

The current was adjusted to between 4.5 and 6 V with a current density of 9 to 12.5 mA/cm$^2$. The gases produced were washed with water and then with concentrated sulfuric acid and the triflyl fluoride was collected in a trap cooled to −70° C. The overall yield is about 80%. identical to steps (d') to (i') of Example 2

Steps d'' to i'':

The invention claimed is:

1. A process for preparing an aqueous solution of sulfonimide compound of formula $(Rf^1—SO_2)(Rf^2—SO_2)NH$, $Rf^1$ and $Rf^2$ being chosen, independently of each other, from the group consisting of: a fluorine atom and groups containing from 1 to 10 carbon atoms chosen from perfluoroalkyl, fluoroalkyl, fluoroalkenyl and fluoroallyl groups, the process comprising a step of oxidizing a mixture M1, wherein mixture M1 comprises $(Rf^1—SO_2)(Rf^2—SO_2)NH$, $Rf^1SO_2H$ and/or $Rf^2SO_2H$, $Rf^1SO_2NH_2$ and/or $Rf^2SO_2NH_2$, with an oxidizing agent, to obtain a mixture M2 comprising $(Rf^1—SO_2)(Rf^2—SO_2)NH$, $Rf^1SO_3H$ and/or $Rf^2SO_3H$, and $Rf^1SO_2NH_2$ and/or $Rf^2SO_2NH_2$.

2. The process according to claim 1, further comprising subjecting the mixture M2 to a distillation step in aqueous medium to separate $(Rf^1—SO_2)(Rf^2—SO_2)NH$ from $Rf^1SO_3H$ and/or from $Rf^2SO_3H$, and from $Rf^1SO_2NH_2$ and/or $Rf^2SO_2NH_2$.

3. A process for preparing an aqueous solution of sulfonimide compound of formula $(Rf^1—SO_2)(Rf^2—SO_2)NH$, $Rf^1$ and $Rf^2$ being chosen, independently of each other, from the group consisting of: a fluorine atom and groups containing from 1 to 10 carbon atoms being chosen from perfluoroalkyl, fluoroalkyl, fluoroalkenyl and fluoroallyl groups, the process comprising:

i) a step of oxidizing a mixture M1, wherein the mixture M1 comprises $(Rf^1—SO_2)(Rf^2—SO_2)NH$ and $Rf^1SO_2H$ and/or $Rf^2SO_2H$, with an oxidizing agent, to obtain a mixture M2 comprising $(Rf^1—SO_2)(Rf^2—SO_2)NH$ and $Rf^1SO_3H$ and/or $Rf^2SO_3H$; and ii) a step of distilling the mixture M2, in aqueous medium, to separate $(Rf^1—SO_2)(Rf^2—SO_2)NH$ from $Rf^1SO_3H$ and/or from $Rf^2SO_3H$.

4. The process according to claim 2, wherein the distillation step is performed in a distillation apparatus comprising a boiler in which the boiler temperature ranges from 50° C. to 300° C.

5. The process according to claim 2, wherein the distillation step is performed in a distillation apparatus comprising a distillation column in which the temperature at the top of the column ranges from 20° C. to 180° C.

6. The process according to claim 2, wherein the distillation step is performed in a distillation apparatus comprising a distillation column, in which the pressure in said distillation column is from 1 to 1000 mbar.

7. The process according to claim 1, wherein the mixture M1 is obtained by distillation of a mixture M'1 comprising $(Rf^1—SO_2)(Rf^2—SO_2)NH$ and $Rf^1SO_2H$ and/or $Rf^2SO_2H$.

8. The process according to claim 7, wherein the sulfonimide $(Rf^1—SO_2)(Rf^2—SO_2)NH$ present in the mixture M'1 is obtained via a step of acidification of an organic phase comprising a complex $(Rf^1—SO_2)(Rf^2—SO_2)NH,NR'_3$, R' representing a linear or branched alkyl group containing from 1 to 20 carbon atoms.

9. The process according to claim 8, wherein the complex $(Rf^1—SO_2)(Rf^2—SO_2)NH,NR'_3$ is obtained via a step of ammonolysis of $Rf^1SO_2X$ and of $Rf^2SO_2X$, X representing Cl, Br or F, $Rf^1$ and $Rf^2$ being chosen, independently of each other, from the group consisting of: a fluorine atom and groups containing from 1 to 10 carbon atoms chosen from perfluoroalkyl, fluoroalkyl, fluoroalkenyl and fluoroallyl groups.

10. The process according to claim 9, wherein $Rf^1SO_2X$ is obtained via a step of oxidation of a mixture M3 comprising $Rf^1CO_2M^a$, $M^a$ representing an alkali metal, and $Rf^1SO_2M^a$, to obtain a two-phase mixture M4, said mixture M4 comprising $Rf^1SO_2X$ and $Rf^1CO_2M^a$.

11. The process according to claim 10, wherein $Rf^1SO_2X$, with X = F, is obtained by electrofluorination of $R^hSO_2F$, $R^h$ representing a hydrocarbon-based chain identical to that of $Rf^1$, said chain comprising hydrogen atoms in place of the fluorine atoms, and $R^hSO_2F$ optionally being obtained from $R^hSO_2W$, with W = Cl, Br or I.

12. The process according to claim 10, wherein the mixture M3 is obtained by:

a step of sulfination of $Rf^1CO_2M^a$ in an organic solvent, to give a mixture M comprising $Rf^1SO_2M^a$ and said organic solvent; and then a step of distillation of said organic solvent from the mixture M, to obtain the mixture M without said solvent; and then a step of separation of the salts of the mixture M derived from the distillation step, optionally, $Rf^1CO_2M^a$ being obtained via a step of salification of $Rf^1CO_2H$.

13. A process for preparing $(Rf^1—SO_2)(Rf^2—SO_2)NM^b$, $M^b$ representing an alkali metal, the process comprising preparing an aqueous solution of $(Rf^1—SO_2)(Rf^2—SO_2)NH$ according to the process as defined in claim 1, optionally neutralizing the aqueous solution of $(Rf^1—SO_2)(Rf^2—SO_2)NH$ in the presence of an alkali metal base, optionally followed by a drying step.

14. A process for preparing $(Rf^1—SO_2)(Rf^2—SO_2)NM^b$, comprising the following steps:

a step a) of salification of $Rf^1CO_2H$ to $Rf^1CO_2M^a$;

a step b) of sulfination of $Rf^1CO_2M^a$ to $Rf^1SO_2M^a$;

a step c) of oxidation of $Rf^1SO_2M^a$ to $Rf^1SO_2X$;

a step d) of ammonolysis of $Rf^1SO_2X$, in the presence of base $NR'_3$ and of $Rf^2SO_2X$ or $Rf^2SO_2NH_2$, to $(Rf^1SO_2)(Rf^2—SO_2)NH,NR'_3$, wherein R' represents a linear or branched alkyl group containing from 1 to 20 carbon atoms, and wherein X represents Cl, Br or F;

a step e) of acidification of $(Rf^1SO_2)(Rf^2SO_2)NH,NR'_3$ to $(Rf^1SO_2)(Rf^2SO_2)NH$;

a step g) of neutralization, with an alkali metal base, of $(Rf^1SO_2)(Rf^2SO_2)NH$ to $(Rf^1—SO_2)(Rf^2—SO_2)NM^b$; and optionally, a step h) of drying of $(Rf^1SO_2)(Rf^2SO_2)NM^b$, in which $(Rf^1—SO_2)(Rf^2—SO_2)NH$, obtained after step e), is in the form of a mixture M1 comprising $(Rf^1—SO_2)(Rf^2—SO_2)NH$, $Rf^1SO_2H$ and/or $Rf^2SO_2H$, $Rf^1SO_2NH_2$ and/or $Rf^2SO_2NH_2$, and said mixture M1, before step g), is subjected to a step i) of oxidation of the mixture M1 with an oxidizing agent to obtain a mixture M2 comprising $(Rf^1—SO_2)Rf^2—SO_2)NH$, $Rf^1SO_3H$ and/or $Rf^2SO_3H$, and $Rf^1SO_2NH_2$ and/or $Rf^2SO_2NH_2$, and said mixture M2 is subjected to a step ii) of distillation of the mixture M2 in aqueous medium, $Rf^1$ and $Rf^2$ being chosen, independently of each other, from the group consisting of: a fluorine atom and groups containing from 1 to 10 carbon atoms being chosen from perfluoroalkyl, fluoroalkyl, fluoroalkenyl and fluoroallyl groups; and $M^a$ and $M^b$ representing, independently of each other, an alkali metal; or comprising the following steps:

a step b') of converting $R^hSO_2W$, with W representing Br, Cl or I, into $R^hSO_2F$;

a step c') of electrofluorination of $R^hSO_2F$ to $Rf^1SO_2F$;

a step d) of ammonolysis of $Rf^1SO_2F$, in the presence of base $NR'_3$ and of $Rf^2SO_2X$ or $Rf^2SO_2NH_2$, to $(Rf^1SO_2)(Rf^2-SO_2)NH,NR'_3$, wherein R' represents a linear or branched alkyl group containing from 1 to 20 carbon atoms, and wherein X represents Cl, Br or F;

a step e) of acidification of $(Rf^1SO_2)(Rf^2SO_2)NH,NR'_3$ to $(Rf^1SO_2)(Rf^2SO_2)NH$;

a step g) of neutralization, with an alkali metal base, of $(Rf^1SO_2)(Rf^2SO_2)NH$ to $(Rf^1-SO_2)(Rf^2-SO_2)NM^b$; and optionally, a step h) of drying of $(Rf^1SO_2)(Rf^2SO_2)NM^b$, in which $(Rf^1-SO_2)(Rf^2-SO_2)NH$, obtained after step e), is in the form of a mixture M1 comprising $(Rf^1-SO_2)(Rf^2-SO_2)NH$, $Rf^1SO_2H$ and/or $Rf^2SO_2H$, $Rf^1SO_2NH_2$ and/or $Rf^2SO_2NH_2$, and said mixture M1, before step g), is subjected to a step i) of oxidation of the mixture M1 with an oxidizing agent to obtain a mixture M2 comprising $(Rf^1-SO_2)$ $Rf^2-SO_2)NH$, $Rf^1SO_3H$ and/or $Rf^2SO_3H$, and $Rf^1SO_2NH_2$ and/or $Rf^2SO_2NH_2$, and said mixture M2 is subjected to a step ii) of distillation of the mixture M2 in aqueous medium, $Rf^1$ and $Rf^2$ being chosen, independently of each other, from the group consisting of: a fluorine atom and groups containing from 1 to 10 carbon atoms being chosen from perfluoroalkyl, fluoroalkyl, fluoroalkenyl and fluoroallyl groups; and $M^b$ representing an alkali metal, and $R^h$ representing a hydrocarbon-based chain identical to that of $Rf^1$, said chain comprising hydrogen atoms in place of the fluorine atoms.

15. The process according to claim 6, wherein the distillation column comprises from 2 to 40 theoretical plates.

16. The process according to claim 6, wherein the distillation column comprises from 4 to 20 theoretical plates.

17. The process according to claim 1, wherein the sulfonimide compound $(Rf^1SO_2)(Rf^2SO_2)NH$ is a symmetrical sulfonimide selected from the group consisting of: $(CF_3SO_2)_2NH$, $(CHF_2SO_2)_2NH$, $(CH_2FSO_2)_2NH$, $(C_2F_5SO_2)_2NH$, $(C_3F_7SO_2)_2NH$, $(FSO_2)_2NH$, and $(C_4F_9SO_2)_2NH$ or a dissymmetrical sulfonimide selected chosen from the group consisting of: $(FSO_2)(CF_3SO_2)NH$, $(FSO_2)(C_2F_5SO_2)NH$, $(FSO_2)(C_3F_7SO_2)NH$, $(FSO_2)(C_4F_9SO_2)NH$, $(CF_3SO_2)(C_2F_5SO_2)NH$, $(CF_3SO_2)(C_3F_7SO_2)NH$, $(CF_3SO_2)(C_4F_9SO_2)NH$, $(C_2F_5SO_2)(C_3F_7SO_2)NH$, $(C_2F_5SO_2)(C_4F_9SO_2)NH$ and $(C_3F_7SO_2)(C_4F_9SO_2)NH$.

18. The process according to claim 3, wherein the sulfonimide compound $(Rf^1SO_2)(Rf^2SO_2)NH$ is a symmetrical sulfonimide selected from the group consisting of: $(CF_3SO_2)_2NH$, $(CHF_2SO_2)_2NH$, $(CH_2FSO_2)_2NH$, $(C_2F_5SO_2)_2NH$, $(C_3F_7SO_2)_2NH$, $(FSO_2)_2NH$ and $(C_4F_9SO_2)_2NH$ or a dissymmetrical sulfonimide selected chosen from the group consisting of: $(FSO_2)(CF_3SO_2)NH$, $(FSO_2)(C_2F_5SO_2)NH$, $(FSO_2)(C_3F_7SO_2)NH$, $(FSO_2)(C_4F_9SO_2)NH$, $(CF_3SO_2)(C_2F_5SO_2)NH$, $(CF_3SO_2)(C_3F_7SO_2)NH$, $(CF_3SO_2)(C_4F_9SO_2)NH$, $(C_2F_5SO_2)(C_3F_7SO_2)NH$, $(C_2F_5SO_2)(C_4F_9SO_2)NH$ and $(C_3F_7SO_2)(C_4F_9SO_2)NH$.

19. The process according to claim 13, wherein $(Rf^1SO_2)(Rf^2SO_2)NM^b$ is a symmetrical salt selected from the group consisting of: $(CF_3SO_2)_2NM^b$, $(CHF_2SO_2)_2NM^b$, $(CH_2FSO_2)_2NM^b$, $(C_2F_5SO_2)_2NM^b$, $(C_3F_7SO_2)_2NM^b$, $(FSO_2)_2NM^b$, and $(C_4F_9SO_2)_2NM^b$, or a dissymmetrical salt selected from: $(FSO_2)(CF_3SO_2)NM^b$, $(FSO_2)(C_2F_5SO_2)NM^b$, $(FSO_2)(C_3F_7SO_2)NM^b$, $(FSO_2)(C_4F_9SO_2)NM^b$, $(CF_3SO_2)(C_2F_5SO_2)NM^b$, $(CF_3SO_2)(C_3F_7SO_2)NM^b$, $(CF_3SO_2)(C_4F_9SO_2)NM^b$, $(C_2F_5SO_2)(C_3F_7SO_2)NM^b$, $(C_2F_5SO_2)(C_4F_9SO_2)NM^b$, $(C_3F_7SO_2)(C_4F_9SO_2)NM^b$.

20. The process according to claim 14, wherein $(Rf^1SO_2)(Rf^2SO_2)NM^b$ is a symmetrical salt selected from the group consisting of:

$(CF_3SO_2)_2NM^b$, $(CHF_2SO_2)_2NM^b$, $(CH_2FSO_2)_2NM^b$, $(C_2F_5SO_2)_2NM^b$, $(C_3F_7SO_2)_2NM^b$, $(FSO_2)_2NM^b$, and $(C_4F_9SO_2)_2NM^b$, or a dissymmetrical salt selected from: $(FSO_2)(CF_3SO_2)NM^b$, $(FSO_2)(C_2F_5SO_2)NM^b$, $(FSO_2)(C_3F_7SO_2)NM^b$, $(FSO_2)(C_4F_9SO_2)NM^b$, $(CF_3SO_2)(C_2F_5SO_2)NM^b$, $(CF_3SO_2)(C_3F_7SO_2)NM^b$, $(CF_3SO_2)(C_4F_9SO_2)NM^b$, $(C_2F_5SO_2)(C_3F_7SO_2)NM^b$, $(C_2F_5SO_2)(C_4F_9SO_2)NM^b$, $(C_3F_7SO_2)(C_4F_9SO_2)NM^b$.

* * * * *